(12) United States Patent
Cashman

(10) Patent No.: US 11,419,818 B2
(45) Date of Patent: Aug. 23, 2022

(54) SYSTEM FOR MANAGING INHALANT AND BREATH ANALYSIS DEVICES

(71) Applicant: Kathryn Cashman, Nashville, TN (US)

(72) Inventor: Kathryn Cashman, Nashville, TN (US)

( * ) Notice: Subject to any disclaimer, the term of this patent is extended or adjusted under 35 U.S.C. 154(b) by 1001 days.

(21) Appl. No.: 15/699,786

(22) Filed: Sep. 8, 2017

(65) Prior Publication Data

US 2018/0028441 A1 Feb. 1, 2018

Related U.S. Application Data

(63) Continuation-in-part of application No. 15/673,276, filed on Aug. 9, 2017, which is a continuation-in-part
(Continued)

(51) Int. Cl.
*A61K 9/00* (2006.01)
*A61M 11/00* (2006.01)
(Continued)

(52) U.S. Cl.
CPC ......... *A61K 9/0078* (2013.01); *A61M 11/005* (2013.01); *A61M 11/041* (2013.01); *A61M 15/0021* (2014.02); *A61M 15/0023* (2014.02); *A61M 15/0065* (2013.01); *A61M 15/0085* (2013.01); *A61N 5/0603* (2013.01); *G16H 10/60* (2018.01); *A61M 11/001* (2014.02); *A61M 15/0025* (2014.02); *A61M 2202/0468* (2013.01); *A61M 2205/3553* (2013.01); *A61M 2205/52* (2013.01); *A61M 2205/587* (2013.01); *A61M 2205/6054* (2013.01); *A61M 2205/8206* (2013.01); *A61M 2209/10* (2013.01); *A61N 2005/0606* (2013.01); *A61N 2005/0651* (2013.01); *A61N 2005/0663* (2013.01); *B05B 17/0646* (2013.01)

(58) Field of Classification Search
None
See application file for complete search history.

(56) References Cited

U.S. PATENT DOCUMENTS 5,950,619 A * 9/1999 van der Linden ........................... A61M 15/0065 128/200.14
6,085,740 A * 7/2000 Ivri ...................... A61M 11/005 128/200.14

(Continued)

*Primary Examiner* — Bradley H Philips
*Assistant Examiner* — Savannah L Gabriel
(74) *Attorney, Agent, or Firm* — Wayne Edwards Ramage; Baker Donelson

(57) ABSTRACT

A computer-based system for receiving, analyzing, processing, managing and sending personal health information, and other information in conjunction with use of one or more personal nebulizer or vaporizing devices and personal breath analysis devices. System devices include a personal nebulizer or vaporizing unit with a mouthpiece, which may be detachable and replaceable. The mouthpiece includes an orifice through which vapor is emitted. The substance to be vaporized is contained in an ampoule inserted into the device, where the substance enters an atomization chamber where vaporization is achieved through piezoelectric transducers or atomizers providing sonic or ultrasonic vibration. The substance includes a variety of therapeutic, homeopathic, or naturopathic formulations, remedies, or serums.

15 Claims, 39 Drawing Sheets

Related U.S. Application Data of application No. 15/587,151, filed on May 4, 2017, now abandoned, which is a continuation-in-part of application No. 15/215,718, filed on Jul. 21, 2016, now abandoned, which is a continuation-in-part of application No. 15/184,761, filed on Jun. 16, 2016.

(60) Provisional application No. 62/384,786, filed on Sep. 8, 2016, provisional application No. 62/372,374, filed on Aug. 9, 2016, provisional application No. 62/331,766, filed on May 4, 2016, provisional application No. 62/302,484, filed on Mar. 2, 2016, provisional application No. 62/194,814, filed on Jul. 21, 2015, provisional application No. 62/180,591, filed on Jun. 16, 2015.

(51) Int. Cl.
*A61M 15/00* (2006.01)
*G16H 10/60* (2018.01)
*A61N 5/06* (2006.01)
*A61M 11/04* (2006.01)
*B05B 17/00* (2006.01)

(56) References Cited

U.S. PATENT DOCUMENTS

| | | | | |
|---|---|---|---|---|
| 6,571,790 | B1* | 6/2003 | Weinstein | A61J 1/00 128/200.14 |
| 7,282,029 | B1* | 10/2007 | Poulsen | A61B 5/14532 600/300 |
| 2002/0129812 | A1* | 9/2002 | Litherland | B05B 17/0646 128/200.14 |
| 2003/0062038 | A1* | 4/2003 | Tanaka | A61M 15/00 128/200.14 |
| 2003/0127538 | A1* | 7/2003 | Patel | A61M 15/0085 239/338 |
| 2003/0140921 | A1* | 7/2003 | Smith | B65D 1/095 128/200.14 |
| 2007/0074722 | A1* | 4/2007 | Giroux | A61M 11/06 128/203.15 |
| 2008/0011292 | A1* | 1/2008 | Sugita | A61M 15/025 128/200.19 |
| 2008/0110452 | A1* | 5/2008 | Kotnik | A61M 11/00 128/200.14 |
| 2010/0089394 | A1* | 4/2010 | Sakurada | A61M 11/001 128/203.14 |
| 2010/0282245 | A1* | 11/2010 | Star | G01N 27/4146 128/200.14 |
| 2013/0167854 | A1* | 7/2013 | Shin | A24F 47/008 131/329 |
| 2013/0269694 | A1* | 10/2013 | Patton | A61M 15/008 128/203.14 |
| 2015/0034076 | A1* | 2/2015 | Dyche | B05B 12/02 128/200.16 |
| 2015/0112707 | A1* | 4/2015 | Manice | G16H 40/63 705/2 |
| 2015/0258370 | A1* | 9/2015 | Arkush | A61B 5/087 482/8 |
| 2015/0330964 | A1* | 11/2015 | Shin | G01N 30/7206 73/23.3 |
| 2016/0022928 | A1* | 1/2016 | Cheng | A61M 15/0025 128/200.14 |
| 2016/0022931 | A1* | 1/2016 | Althorpe | A61M 11/003 128/203.12 |
| 2016/0271343 | A1* | 9/2016 | Abate | A61M 15/02 |
| 2018/0043114 | A1* | 2/2018 | Bowen | A61M 15/003 |

* cited by examiner

USERS

SYSTEM FOR MANAGING INHALANT AND BREATH ANALYSIS DEVICES

This application claims benefit of and priority to U.S. Provisional Application No. 62/384,786, filed Sep. 8, 2016, and also is a continuation-in-part of U.S. patent application Ser. No. 15/673,276, filed Aug. 9, 2017, which claims benefit of and priority to U.S. Provisional Application No. 62/372,374, filed Aug. 9, 2016, and which also is a continuation-in-part application of U.S. patent application Ser. No. 15/587,151, filed May 4, 2017, which claims benefit to U.S. Provisional Application No. 62/331,766, filed May 4, 2016, and which also is a continuation-in-part application of U.S. patent application Ser. No. 15/215,718, filed Jul. 21, 2016, which is a continuation-in-part application of U.S. patent application Ser. No. 15/184,761, filed Jun. 16, 2016, which claims benefit of and priority to U.S. Provisional Applications No. 62/302,484, filed Mar. 2, 2016, No. 62/194,814, filed Jul. 21, 2015, and No. 62/180,591, filed Jun. 16, 2015, and is entitled to those filing dates for priority. The specifications, figures, appendices and complete disclosures of U.S. patent application Ser. Nos. 15/673,276; 15/587,151; 15/215,718; and 15/184,761; and U.S. Provisional Applications Nos. 62/384,786; 62/331,766; 62/302,484; 62/194,814; and 62/180,591 are incorporated herein in their entireties by specific reference for all purposes.

FIELD OF INVENTION

The present invention relates to a system for managing health and related information in connection with use of a personal inhalation device and a personal breath analysis device. More particular, this invention relates to a computer-based system for managing health and related information through use of a handheld vaporizing device for generating a vapor for inhaling by a user, and a handheld breath analysis device for analyzing components of a user's breath.

BACKGROUND OF THE INVENTION

A variety of vaporizers or nebulizers are known in the prior art, particularly for use with tobacco or tobacco extracts. Typically, the substance to be vaporized is heated by the device, and emitted through an opening or orifice. However, such devices do not provide the ability to finely controlled the application of a therapeutic substance, or provide for the calibration and monitoring of treatments using a vaporized therapeutic sub stance.

SUMMARY OF INVENTION

In various embodiments, the present invention comprises a computer-based system for receiving, analyzing, processing, managing and sending personal health information, and other information in conjunction with use of one or more personal nebulizer or vaporizing devices and personal breath analysis devices. The system comprises a health or wellness computer application, program or database on a computer or mobile device (e.g., smart phone, tablet computer), which can coordinate collecting, storing, analyzing, and diagnosing various information obtained from a variety of other devices or sources, such as a breath analysis device that can capture and analyze the content of exhaled air, a health band (e.g., Fit Bit), other detection devices, or information entered into and stored in a separate health or wellness computer application, program or database on a computing device or mobile computing device. The system can use this information to develop health-related recommendations for an individual, including, but not limited to, recommendations for a substance or substances to be used in a personal vaporization device.

In several embodiments, the system comprises a personal nebulizer or vaporizing unit. While referred to herein as a nebulizer or vaporizing unit, the device encompasses devices of all sorts, including but not limited to inhalers, nebulizers, vaporizers, humidifiers, ventilators, or other devices that are used for delivery of any sort of substance into the body via breathing, and includes but is not limited to devices that break up solutions and suspensions into small aerosol droplets for inhalation by a user.

The unit comprises an outer main shell with a mouthpiece unit at one end. The mouthpiece unit may be detachable and replaceable. In addition, the top of the shell may be removable from the base of the shell. The mouthpiece unit comprises an orifice through which vapor is emitted. A mouthpiece cover may be used to cover some or all of the mouthpiece unit. The cover may snap-fit around the perimeter, or a portion of the cover may be inserted into the orifice, or both, to secure the cover in place.

The outer main shell further includes one or more controls, such as a button, slider, or switch, that may be used to turn the unit on or off, or control other functions, as described below. One or more lights, LEDS, or other indicators may be provided to indicate status of the unit, including, but not limited to, power status and operational status. The main shell further comprises an opening with removable cover for insertion of an ampoule or cartridge into the unit. The cartridge holds the substance to be vaporized during operation of the unit. The vaporized substance is inhaled by the user while holding the unit.

The substance to be vaporized may be in the form of a liquid, gel, gas, solid, or the like. In several embodiments, the substance comprises one or more of a therapeutic substance, homeopathic or naturopathic formulations or remedies, serums, or the like. Particular substances may be chosen or selected for particular desired effects, therapies or treatments, and substances have natural vaporization characteristics that are dependent on a variety of factors, including, but not limited to, temperature, air flow, and substance composition and chemical state. Selection of one or more substances for vaporization may be made based upon information obtained from other devices or systems, such as a breath analysis device that can capture and analyze the content of exhaled air, a health band (e.g., Fit Bit), other detection devices, or information stored in or entered into in a health or wellness computer application, program or database on a computer or mobile device (e.g., smart phone, tablet computer), which can coordinate diagnosing this information and developing recommendations for the substance or substances to be used.

In an alternative embodiment, the unit comprises an internal, refillable chamber for holding the substance to be vaporized. The refillable chamber may be filled by insertion of the substance through the opening with removable cover, or other filling port.

In several embodiments, the interior of the inhalation unit comprises a atomization chamber, which receives the substance from the ampoule or refillable chamber through such means as a wick or other conduit. Vaporization is achieved by means of one or more piezoelectric transducers or atomizers, providing sonic or ultrasonic vibration. Vapor is emitted through conduit to the mouthpiece orifice. Calibration and control of the atomization process (e.g., temperature, size of inlet openings, rate of vaporization, timer) may be controlled by the user manually using a control on the unit, automatically controlled based upon a code or symbol (e.g., bar code, QR code, RFID chip) on the ampoule read by a bar code scanner in the device after insertion, or remotely (such as by wireless connection to a computer or mobile device). This calibration and control may be performed according to the diagnosis and recommendations developed in the manner described above.

In several embodiments, the ampoule itself may comprise a piezoelectric unit, and may be multiple use or single use. The ampoule may be hermetically sealed, and made of any suitable material, including, but not limited to, glass, plastic, polymer, metal, or the like. The ampoule may be rigid, or flexible (e.g., a flexible pouch). In one embodiment, the ampoule comprises a barrel shape with a proximal end and distal end, the proximal end being open and extending into a rim or two opposing tabs perpendicular to the axis of the barrel, each tab comprising an ergonomic and/or flat radius section following the extension point of the tab.

The piezoelectric unit may be located in the top of the ampoule, such as in a cap that screws onto or is otherwise attached to the body of the ampoule. The cap may be permanently affixed to the ampoule, such as by welding, gluing, or adhesive, or may be removable. The piezoelectric unit may be held in an insert or holder used to position the piezoelectric unit directly over the opening of the ampoule, thereby providing consistent flow of the material. The piezoelectric unit may be in the form of a wafer or similar configuration. Power may be supplied to the unit by guide wires or connections to a power source in an inhaler unit in which the ampoule is inserted, or by a battery or similar power source attached to or embedded in the ampoule.

Once the piezoelectric unit is removed, or the cap is opened, the integrity of the electronics is destroyed (e.g., the guide wires are broken or torn) to prevent re-use (i.e., the unit can only be used once with the pre-loaded material, and must be discarded after use). This safeguards against the use of illegal drugs, improper medicaments, or the like. The cap also may be secured.

In additional embodiments, the piezoelectric unit may embedded into the side or bottom of the body of the ampoule in middle or bottom positions. The piezoelectric unit may be inaccessible, ensuring that the ampoule is used only once and cannot be refilled. The exterior of the ampoule may be printed directly onto with a description of the contents, a bar or similar code (e.g., QR code), and other information. The ampoule may further comprise a RFID chip.

A circuit board provides control and power functions. Power may be provided by one or more batteries. The battery or batteries may be standard, replaceable batteries, or may be a rechargeable battery built into the unit, and recharged with a recharging cord or similar means. In some embodiments, a power cord and plug may be plugged into a standard electrical outlet to provide power. A wireless or Bluetooth chip provides for wireless communications. A USB, mini-USB, or similar communications port provides for direct communications, and uploading and downloading of programs or data.

Other vaporization means may be provided, such as a heat source (burner, flame, electrical). Temperature may be controlled in the manner of other parameters discussed above. In yet another embodiment, a unit has multiple vaporization elements, and can vaporize different substances from multiple refillable chambers or multiple ampoules simultaneously, in sequence, or some combination thereof.

The unit may have a computer memory storage capability, and store vaporization treatment data so that the details of the vaporization treatment can be subsequently used to evaluate clinical or medical treatment compliance and effectiveness. The information may be provided by wired or wireless connection to a health or wellness program, as described above. The unit may have one or more means of wireless communication (e.g., wireless chip, Bluetooth), and wired communication (e.g., data ports, USB ports).

The atomization chamber and conduit may be cleaned between uses using a cleaning solution, by one or more interior UV light or radiation sources along the chamber and conduit, or combinations thereof.

In yet another embodiment, one or more light sources (such as, but not limited to, light-emitting diodes (LEDs), laser diodes, fiber optics, full spectrum light sources, RGB LEDs, and the like), vibrational sources (ultrasonic or otherwise), heating sources or elements, piezo transducers, or combinations thereof, may be located on or in the mouthpiece unit, or a portion of the device insertable into the mouth, to provide light-related or other therapy to the mouth, lips and gums. Different arrangements (e.g., colors, intensity, locations) of light sources may be provided on different mouthpiece units, which can be interchanged as desired.

DETAILED DESCRIPTION OF EXEMPLARY EMBODIMENTS

In various exemplary embodiments, the present invention comprises a computer-based system for receiving, analyzing, processing, managing and sending personal health information, and other information in conjunction with use of one or more personal nebulizer or vaporizing devices and personal breath analysis devices. As described in detail below, the system comprises a health or wellness computer application, program or database on a computer or mobile device (e.g., smart phone, tablet computer), which can coordinate collecting, storing, analyzing, and diagnosing various information obtained from a variety of other devices or sources, such as a breath analysis device that can capture and analyze the content of exhaled air, a health band (e.g., Fit Bit), other detection devices, or information entered into and stored in a separate health or wellness computer application, program or database on a computing device or mobile computing device. The system can use this information to develop health-related recommendations for an individual, including, but not limited to, recommendations for a substance or substances to be used in a personal vaporization device.

FIGS. 1-4 shows an example of a personal nebulizer or vaporizing unit 2. While referred to herein as a nebulizer or vaporizing unit, the device encompasses devices of all sorts, including but not limited to inhalers, nebulizers, vaporizers, humidifiers, ventilators, or other devices that are used for delivery of any sort of substance into the body via breathing, and includes but is not limited to devices that break up solutions and suspensions into small aerosol droplets for inhalation by a user.

Figure 1:
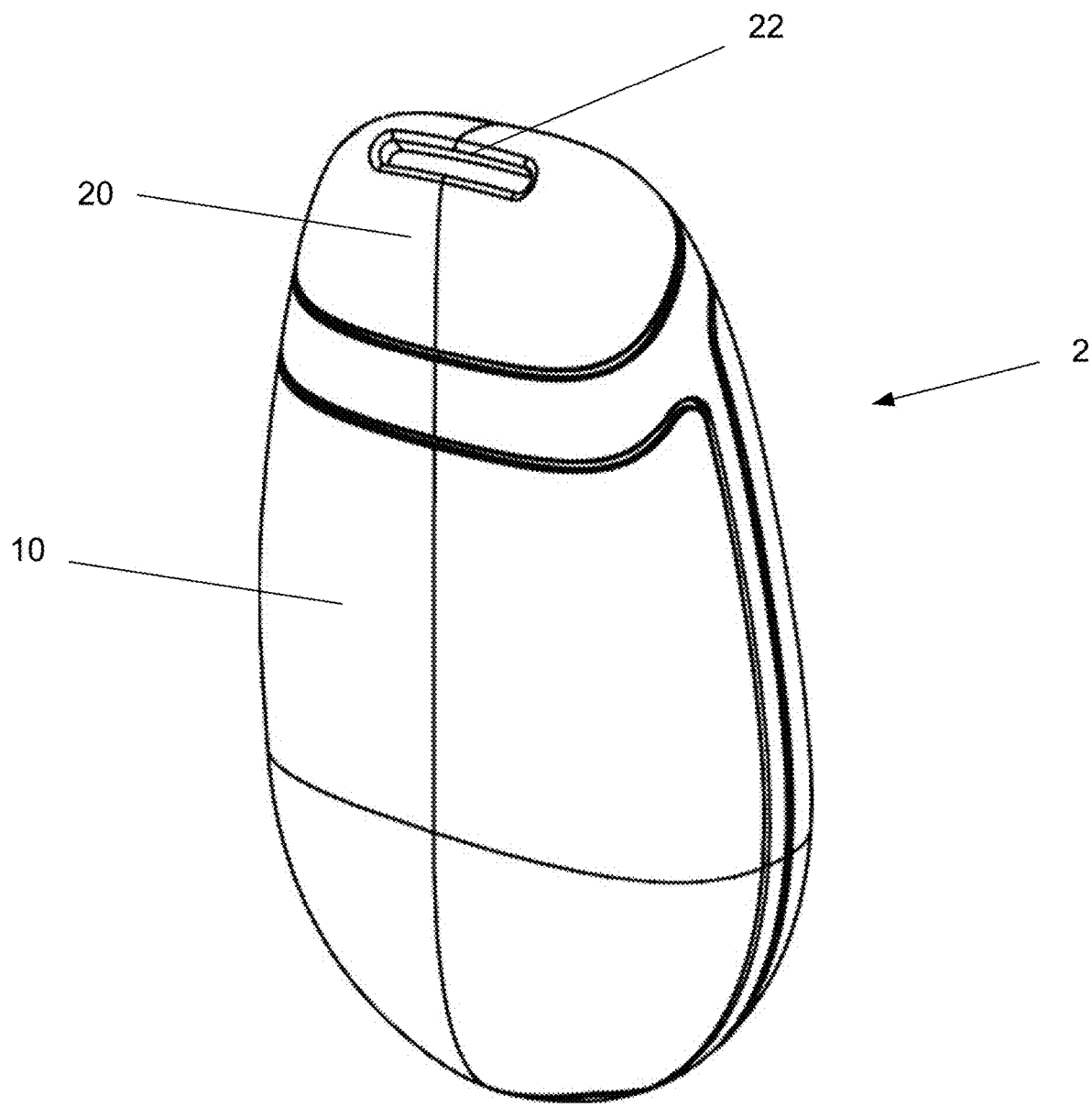
FIG. 1 shows a perspective view of a device in accordance with an embodiment of the present invention.
Figure 2:
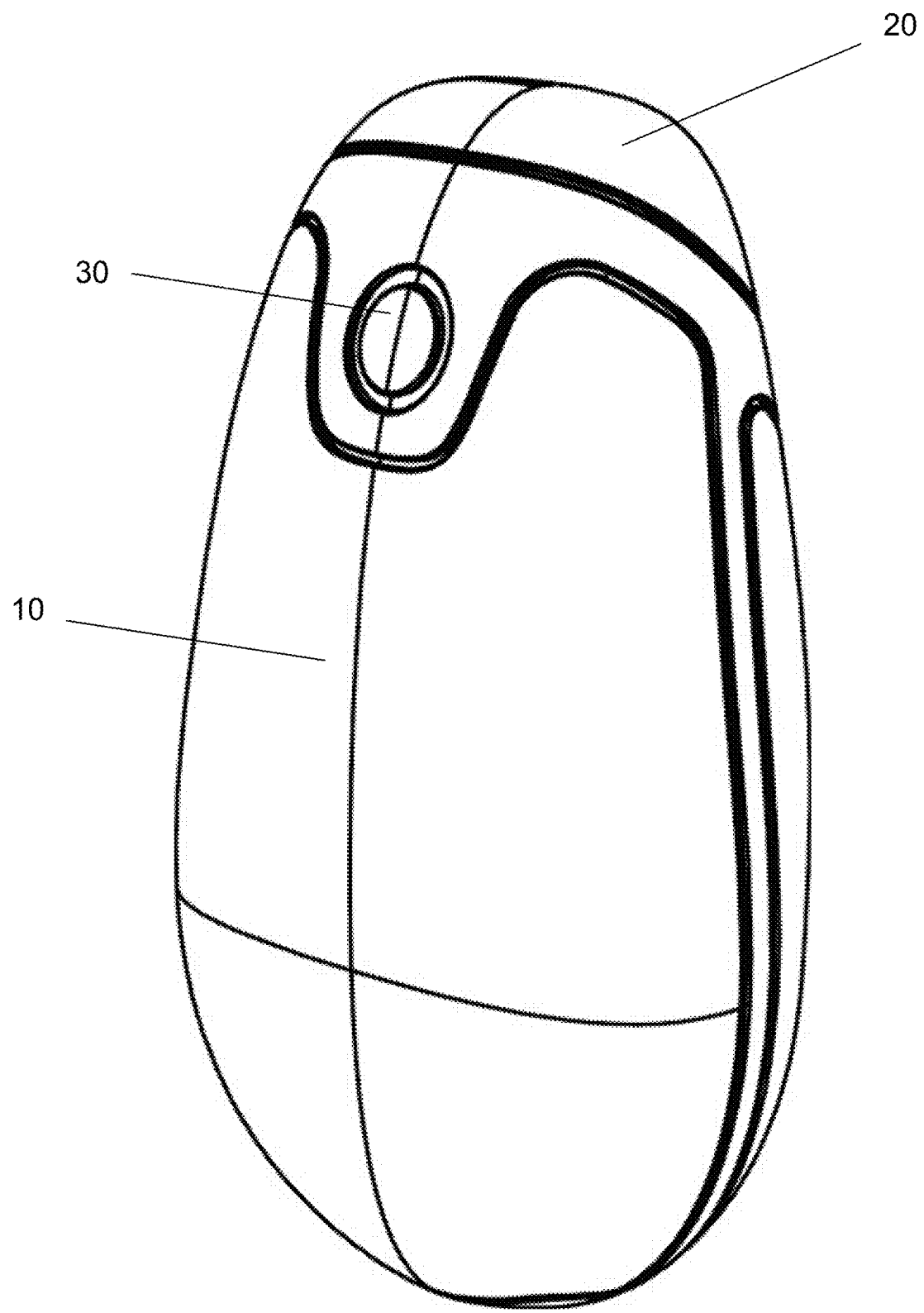
FIG. 2 shows a top perspective view of the device of FIG. 1.
Figure 3:
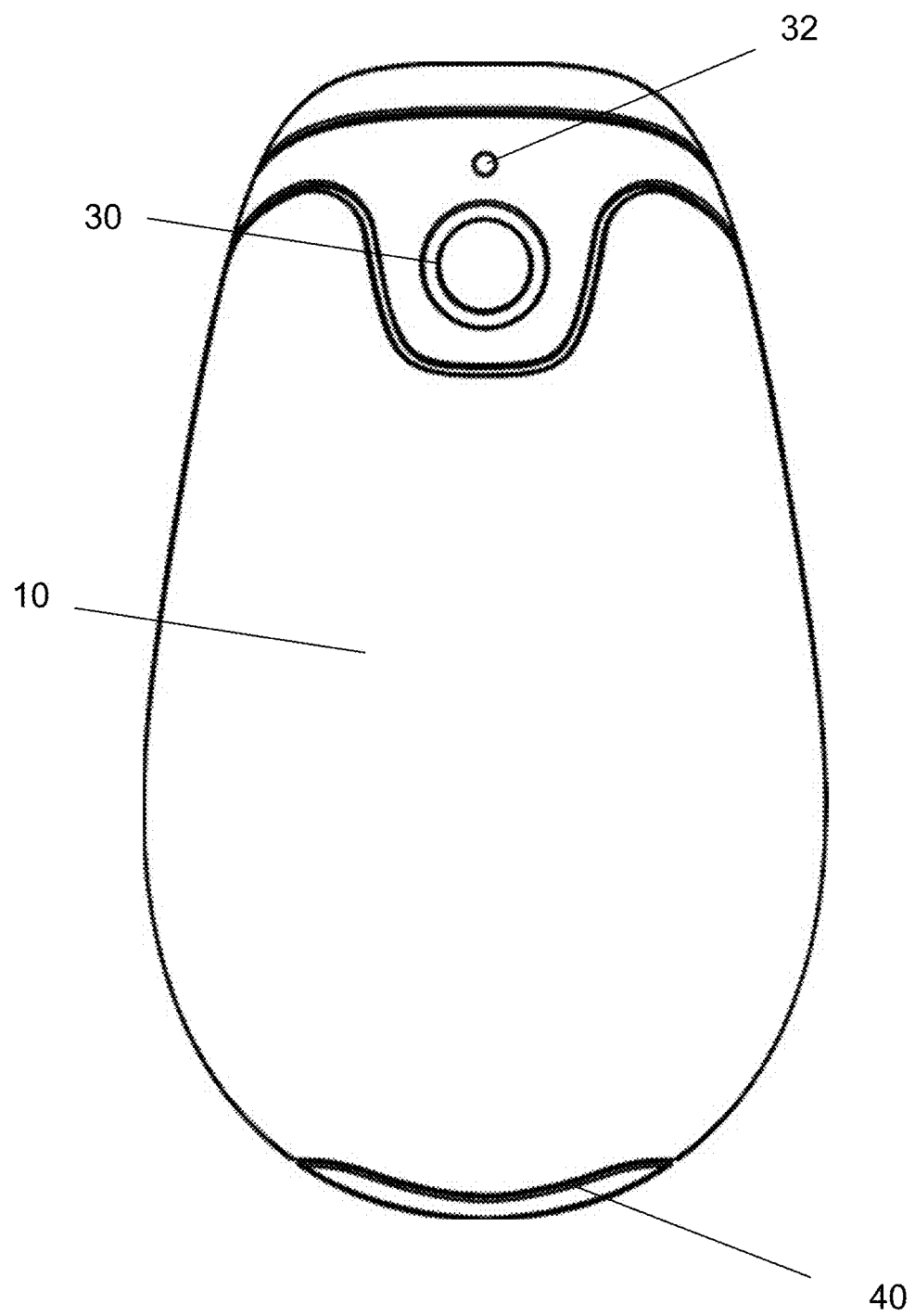
FIG. 3 shows a top view of the device of FIG. 1.
Figure 4:
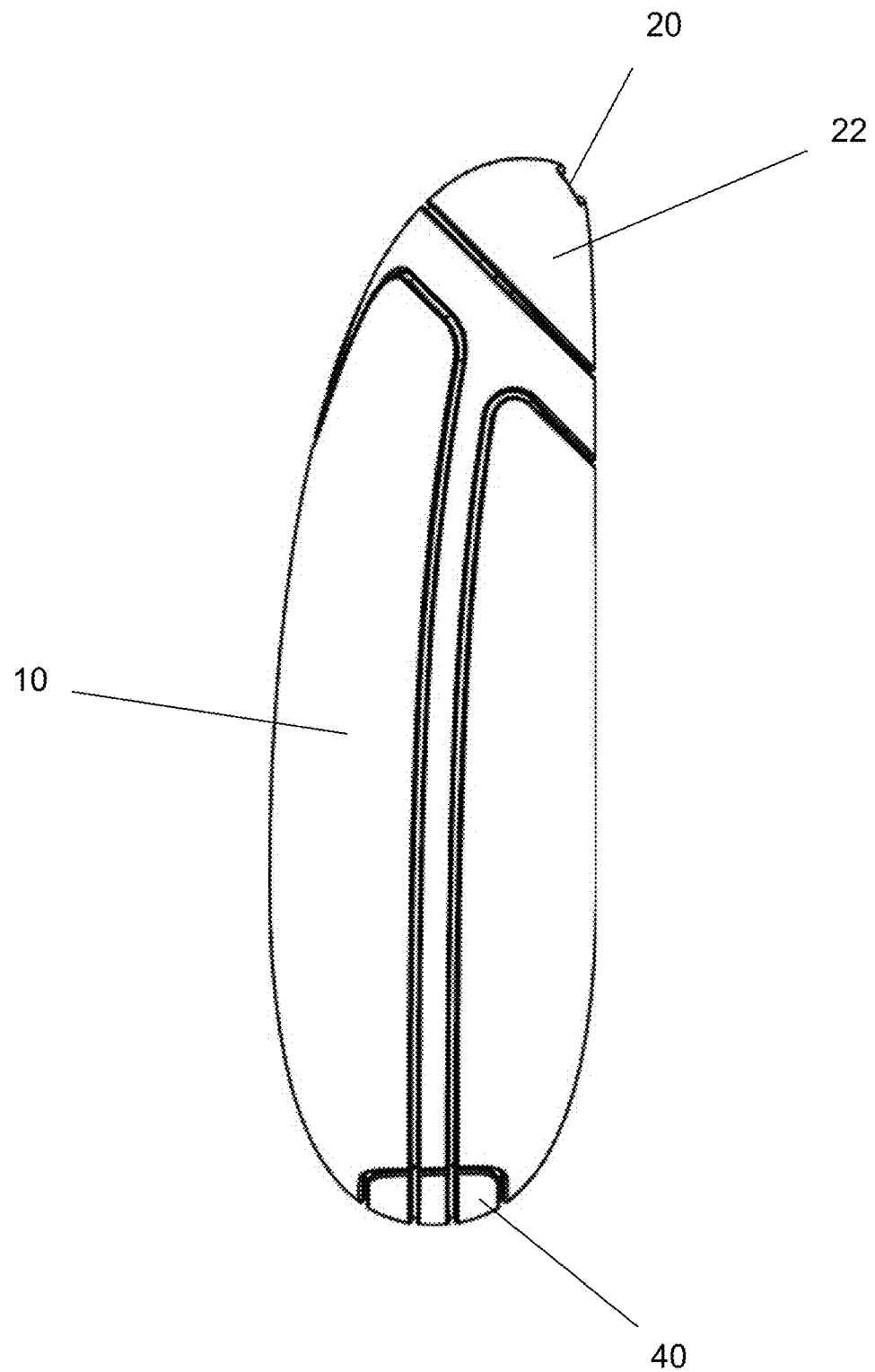
FIG. 4 shows a side view of the device of FIG. 1.
Figure 5:
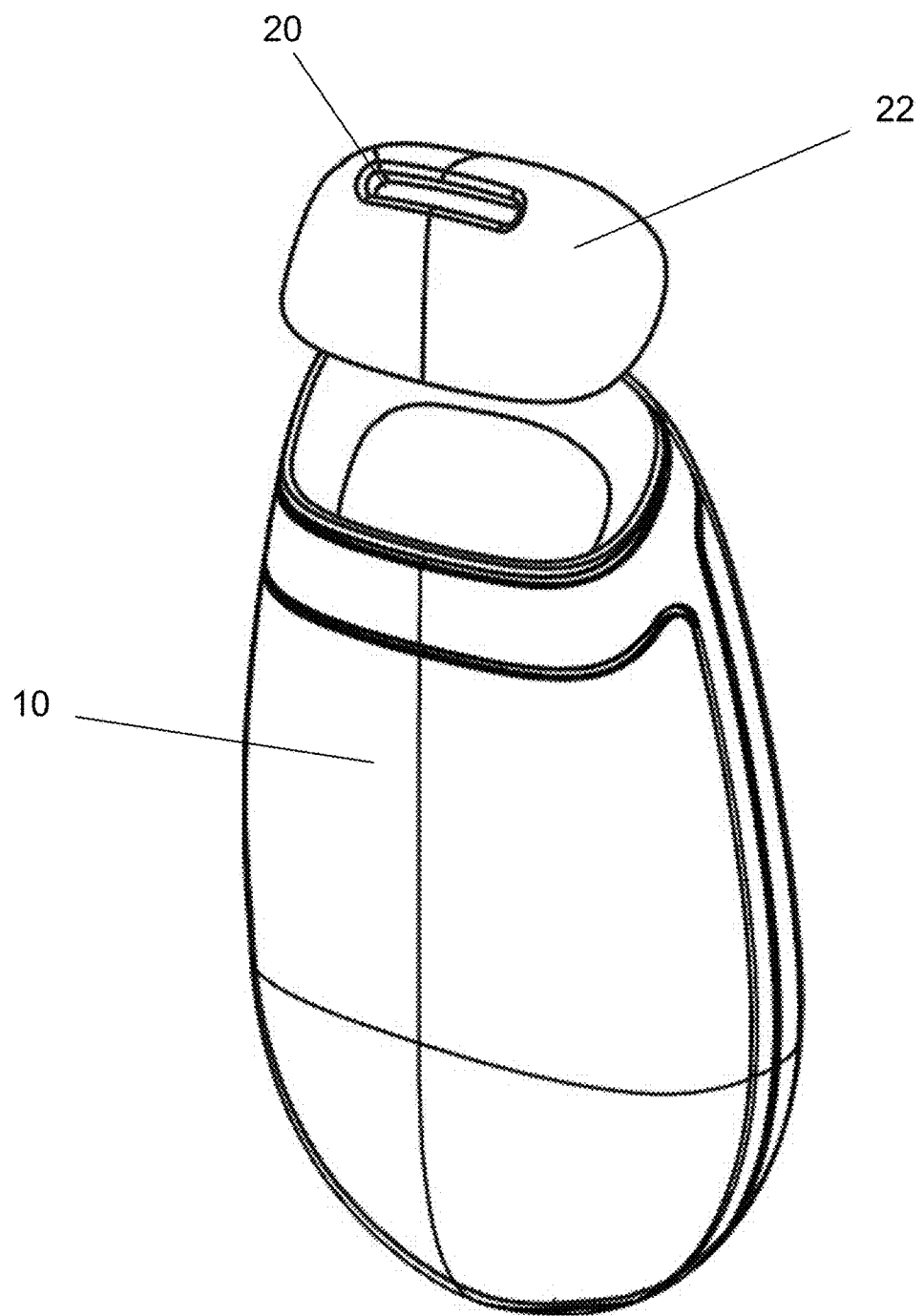
FIG. 5 shows an exploded perspective view of the device of FIG. 1.
Figure 6:
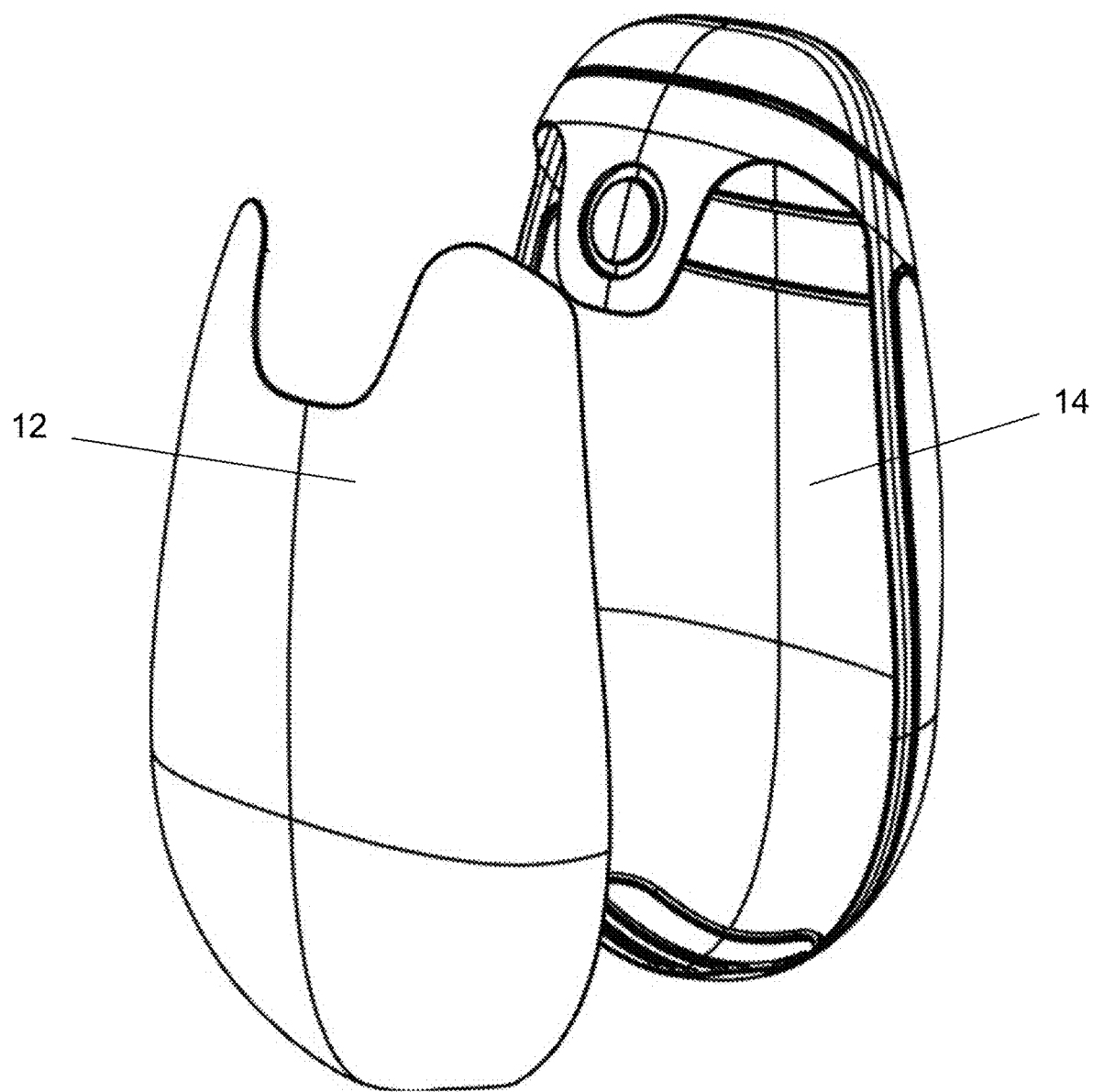
FIG. 6 shows another exploded perspective view of the device of FIG. 1.
Figure 7:
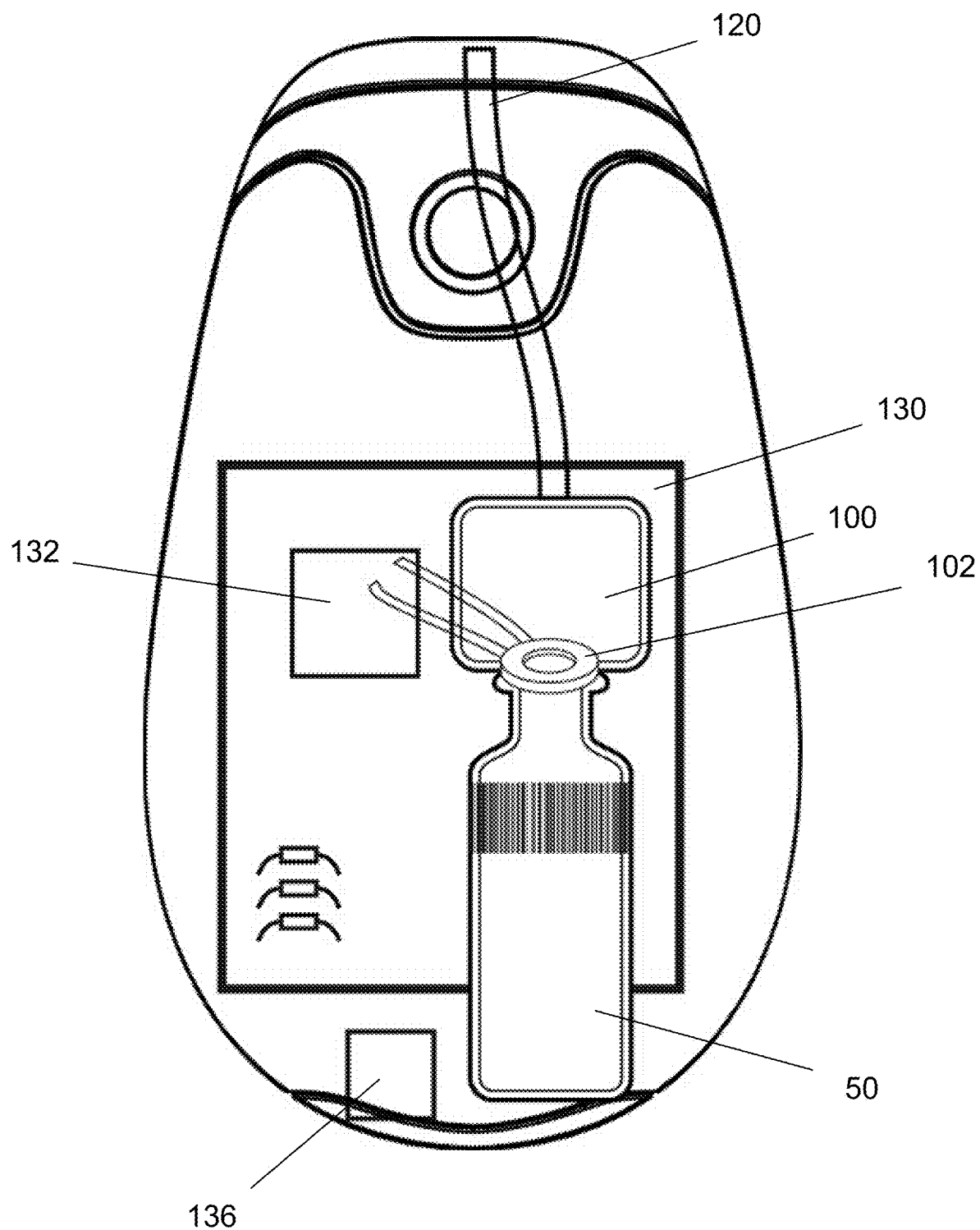
FIG. 7 shows a view of the interior of the device of FIG. 1.
Figure 8:
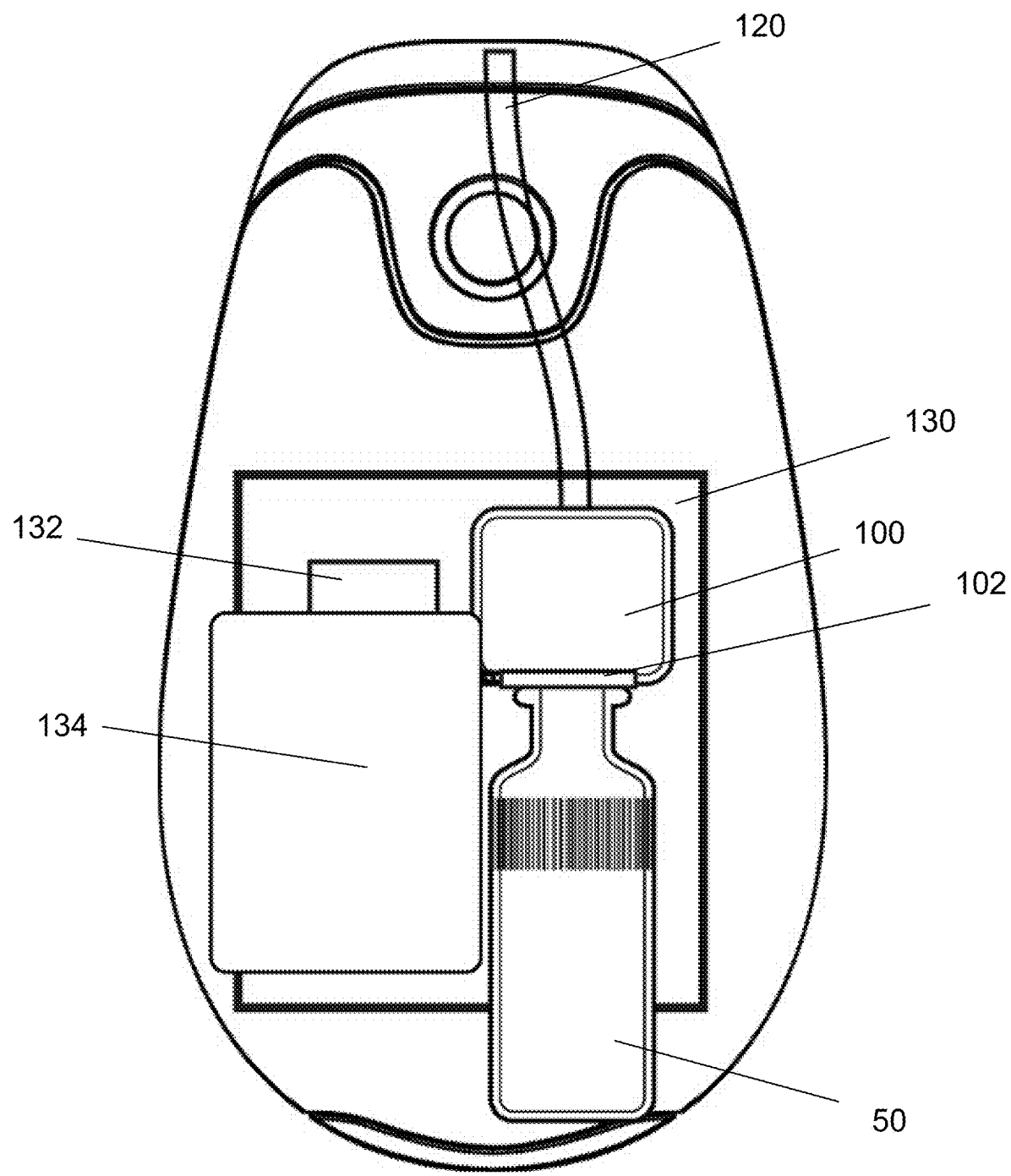
FIG. 8 shows another view of the interior of the device of FIG. 1.
Figure 9:
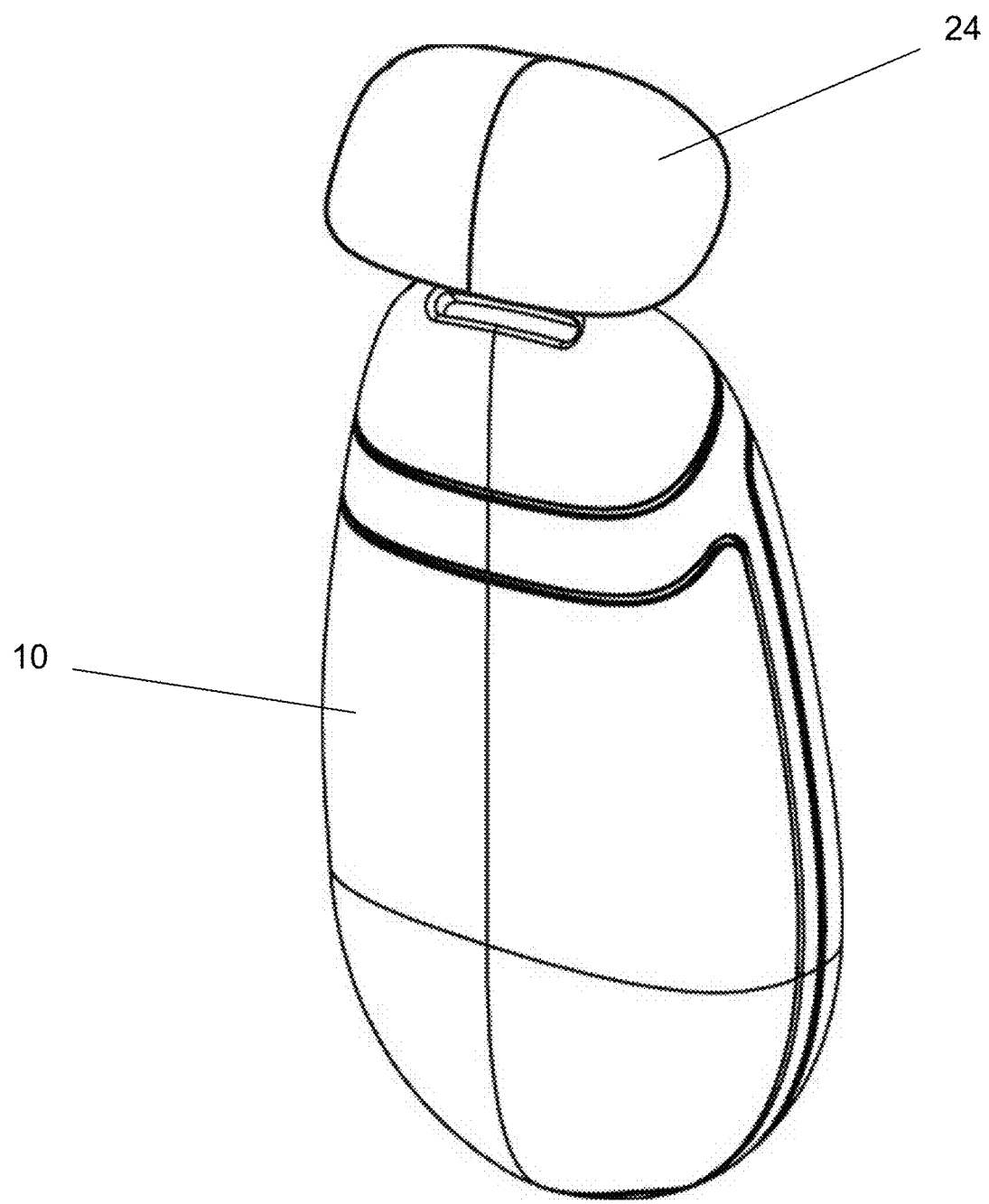
FIG. 9 shows a perspective view of the device of FIG. 1 with a cover.
Figure 10:
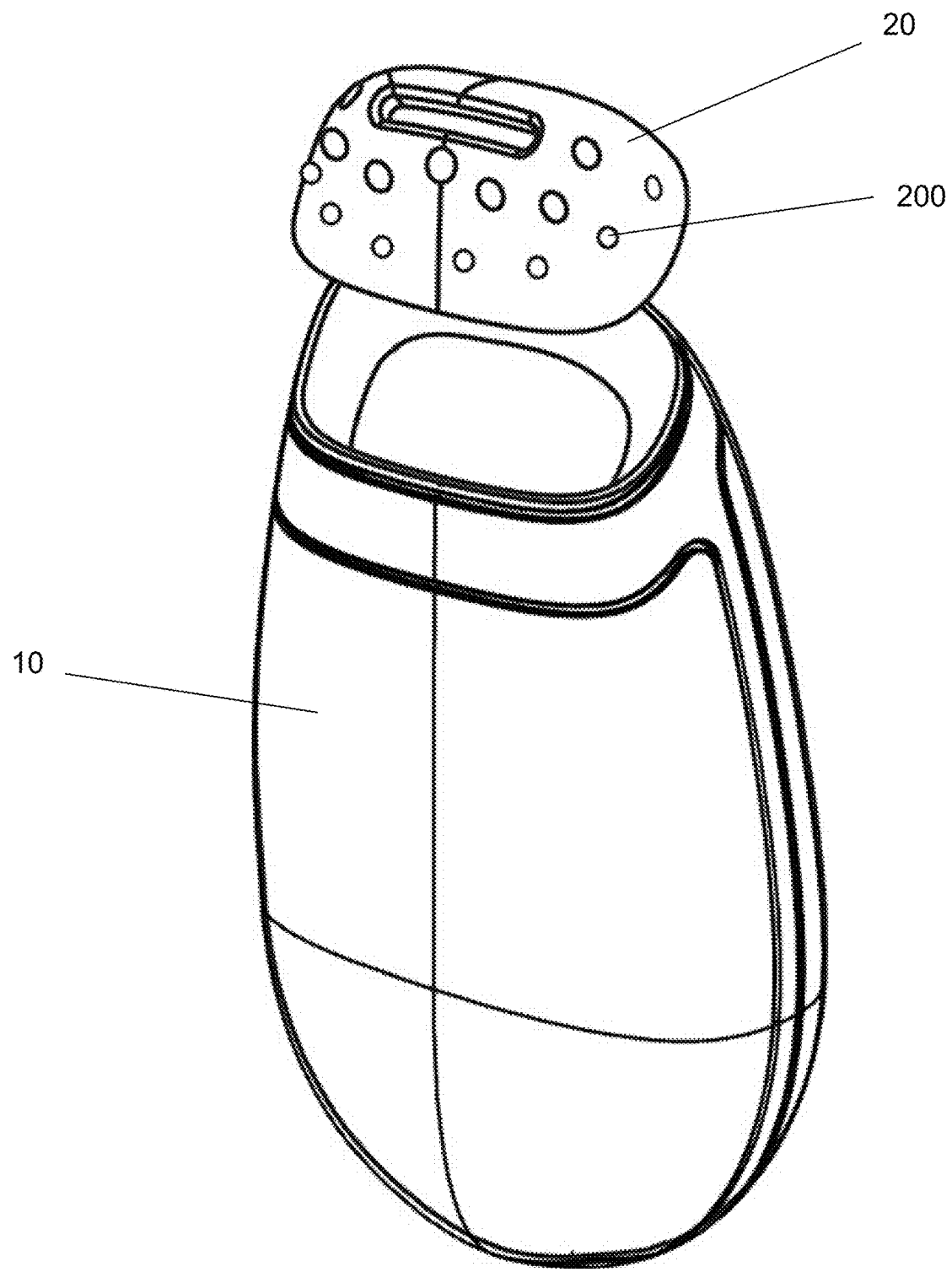
FIG. 10 shows a perspective view of the device of FIG. 1 with exterior light sources.
Figure 11:
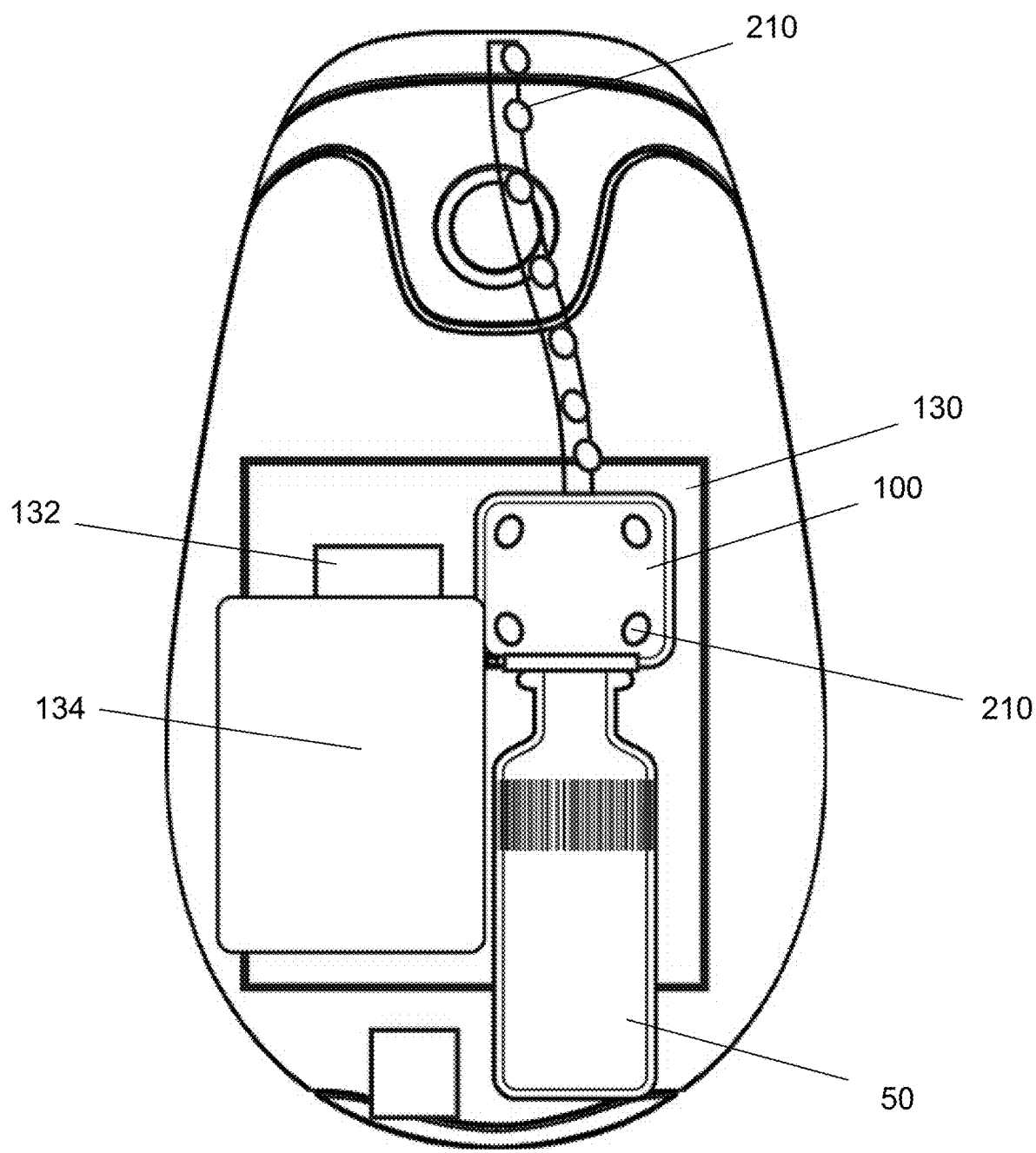
FIG. 11 shows a perspective view of the device of FIG. 1 with interior light sources.
Figure 12:
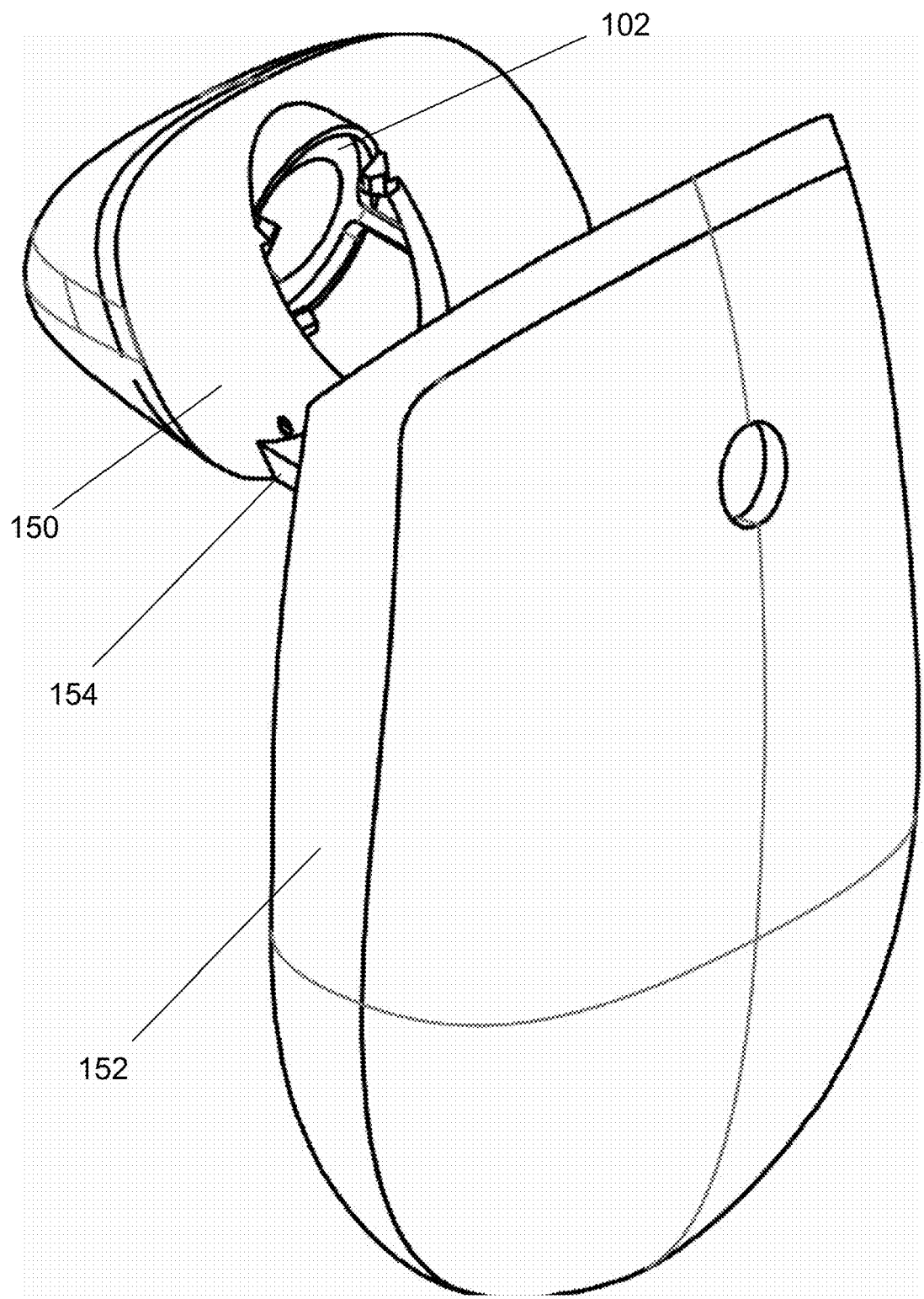
FIGS. 12-14 shows a perspective view of a hinged device in accordance with an embodiment of the present invention.
Figure 13:
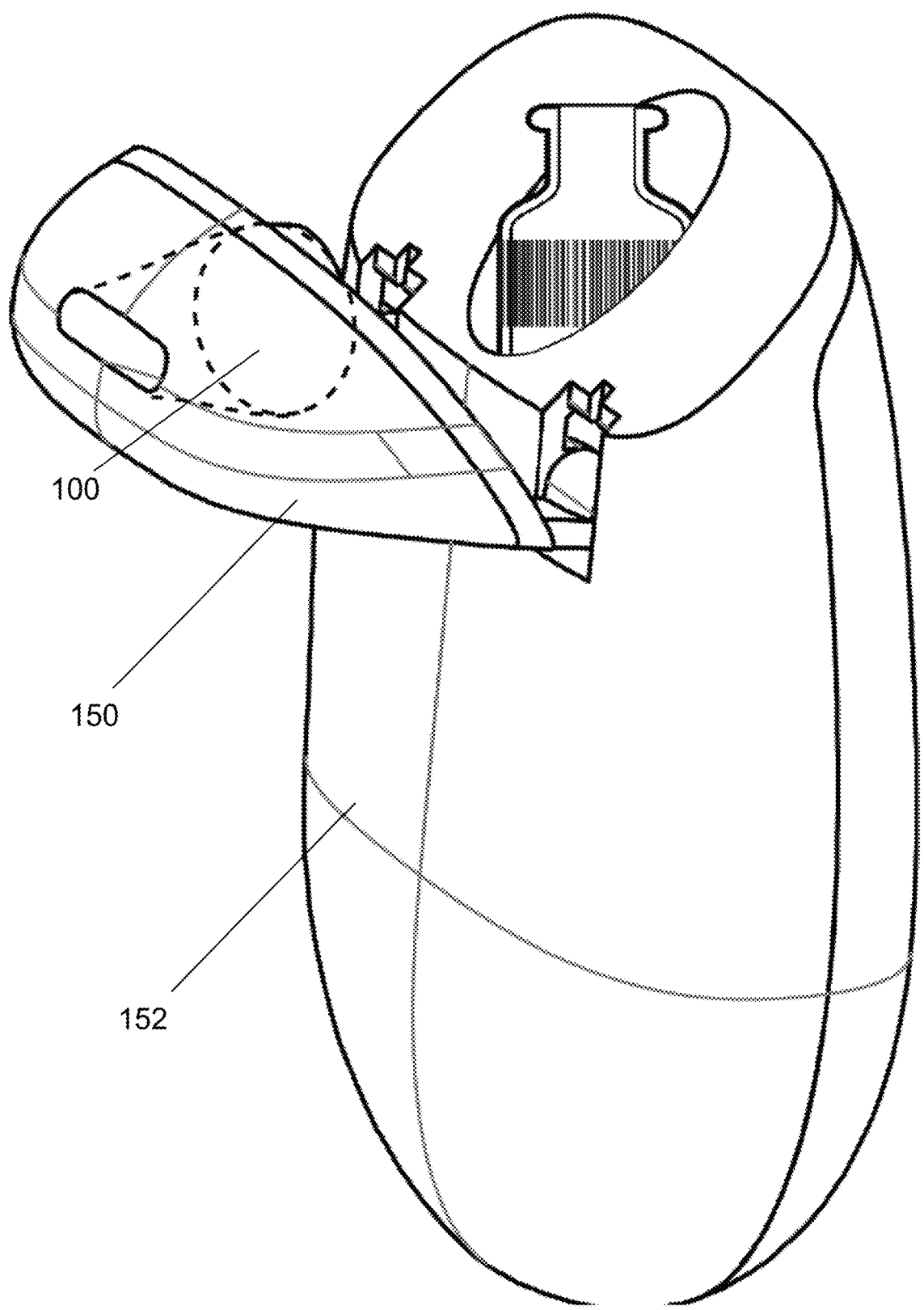
Figure 14:
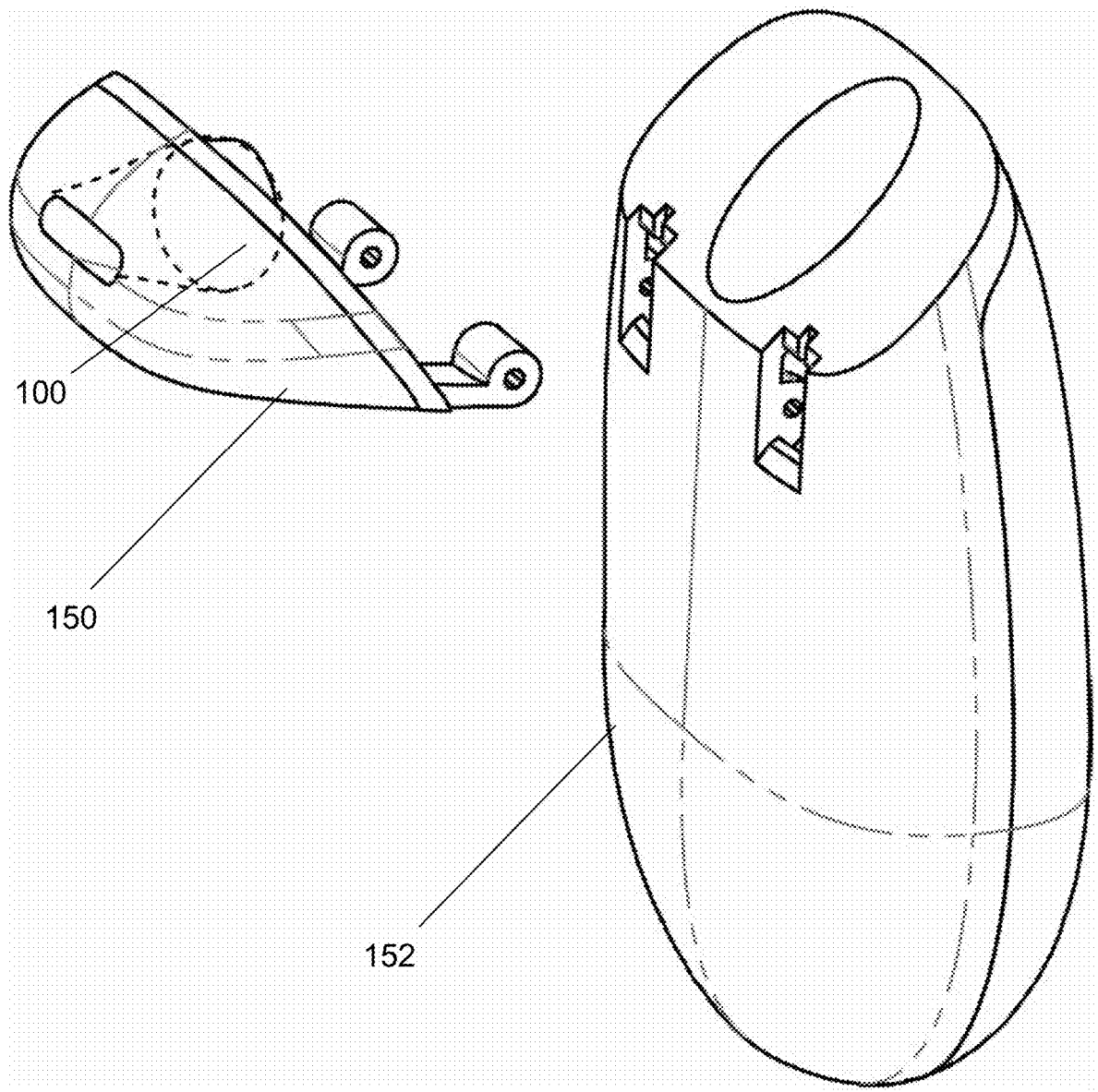
Figure 15:
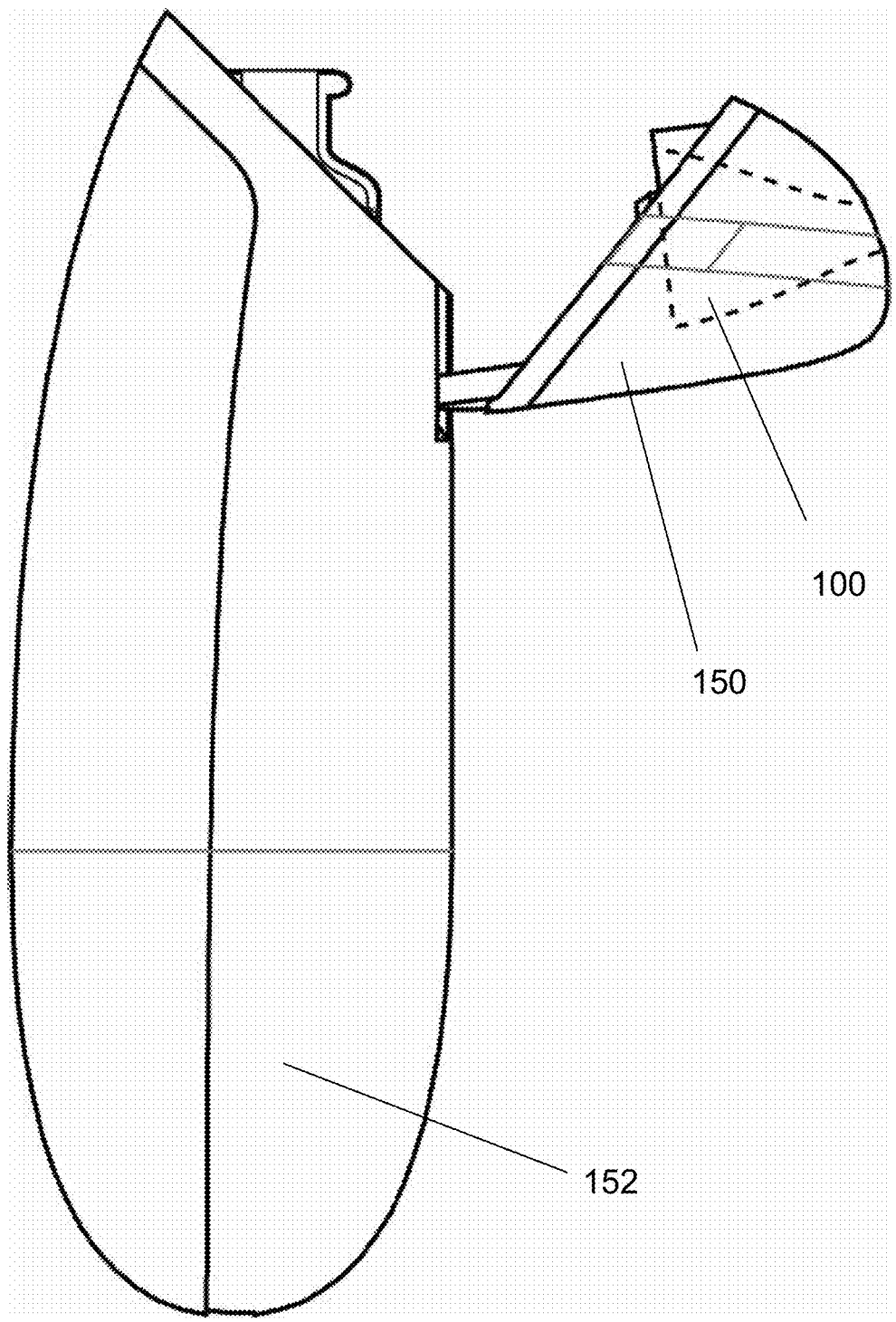
FIG. 15 shows a side view of the device of FIG. 12.
Figure 16:
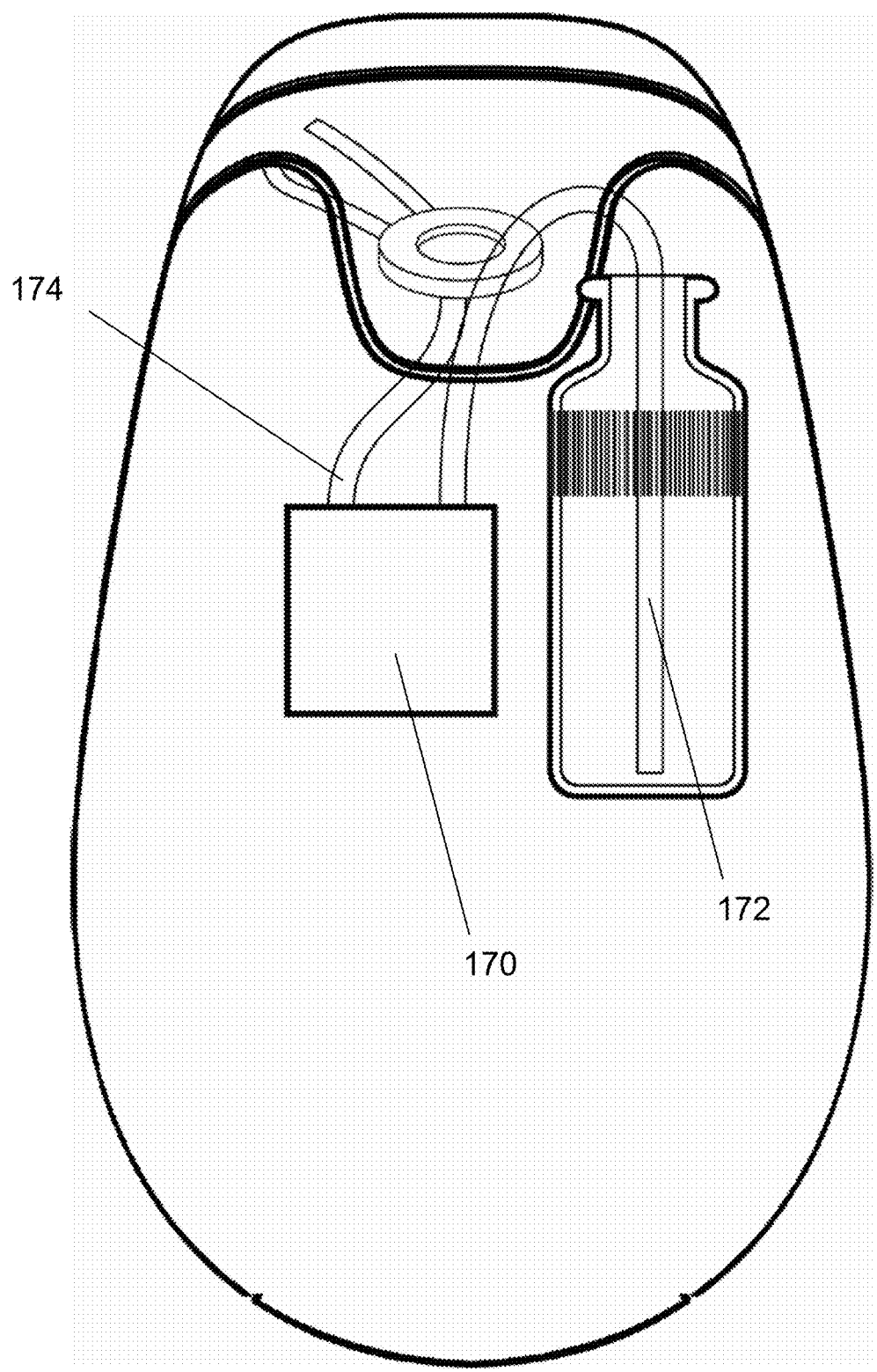
FIG. 16 shows a top cutaway view of the device of FIG. 12.

The unit seen in FIGS. 1-4 comprises a main body with an outer main shell 10, with a mouthpiece unit 20 at one end. The mouthpiece unit may be detachable and replaceable, as seen in FIG. 5. In addition, as seen in FIG. 6, the top 12 of the shell may be removable from the base 14 of the shell. The mouthpiece unit 20 comprises an orifice 22 through which vapor is emitted. A mouthpiece cover 24 may be used to cover some or all of the mouthpiece unit, as seen in FIG. 9. The cover may snap-fit around the perimeter, or a portion of the cover may be inserted into the orifice, or both, to secure the cover in place.

The outer main shell 10 further includes one or more controls 30, such as a button, slider, or switch, that may be used to turn the unit on or off, or control other functions, as described below. One or more lights, LEDS, or other indicators 32 may be provided to indicate status of the unit, including, but not limited to, power status and operational status.

The main shell 10 further comprises an opening with removable cover 40 for insertion of an ampoule or cartridge 50 into an ampoule holding chamber in the unit. The ampoule or cartridge holds the substance to be vaporized during operation of the unit. The vaporized substance is inhaled by the user while holding the unit.

The substance to be vaporized may be in the form of a liquid, gel, gas, solid, or the like. In several embodiments, the substance comprises one or more of a therapeutic substance, homeopathic or naturopathic formulations or remedies, serums, or the like. Particular substances may be chosen or selected for particular desired effects, therapies or treatments, and substances have natural vaporization characteristics that are dependent on a variety of factors, including, but not limited to, temperature, air flow, and substance composition and chemical state. Selection of one or more substances for vaporization may be made based upon information obtained from other devices or systems, such as a breath analysis device that can capture and analyze the content of exhaled air, a health band (e.g., Fit Bit), other detection devices, or information stored in or entered into in a health or wellness computer application, program or database on a computer or mobile device (e.g., smart phone, tablet computer), which can coordinate diagnosing this information and developing recommendations for the substance or substances to be used.

In an alternative embodiment, the unit comprises an internal, refillable chamber for holding the substance to be vaporized. The refillable chamber may be filled by insertion of the substance through the opening with removable cover 40, or other filling port.

As seen in FIGS. 7-11, the interior of the unit comprises a atomization chamber 100, which receives the substance from the ampoule 50 or refillable chamber through such means as a wick or other conduit. In several embodiments, a pump 170 is used to move the substance from the ampoule 50 means of a tube 172 inserted into the ampoule and a tube 174 that delivers the substance for vaporization. Vaporization is achieved by means of one or more piezoelectric transducers or atomizers 102, providing sonic or ultrasonic vibration. The transducers or atomizers may be located in or on various sides of the atomization chamber, at the bottom of the atomization chamber, or just outside the atomization chamber. Vapor is emitted through conduit 120 or an extension of the atomization chamber to the mouthpiece orifice 22.

Calibration and control of the atomization process (e.g., temperature, size of inlet openings, rate of vaporization, timer) may be controlled by the user manually using a control on the unit, automatically controlled based upon a code or symbol (e.g., bar code, QR code, RFID chip) in or on the ampoule, or remotely (such as by wireless connection, or Bluetooth or BLE communications to a computer or mobile device). This calibration and control may be performed according to the diagnosis and recommendations developed in the manner described above.

A circuit board 130 provides control and power functions. Power may be provided by one or more batteries 134. The battery or batteries may be standard, replaceable batteries, or may be a rechargeable battery built into the unit, and recharged with a recharging cord or similar means. In some embodiments, a power cord and plug may be plugged into a standard electrical outlet to provide power. A wireless or Bluetooth chip 132 provides for wireless communications. A USB, mini-USB, or similar communications port 136 provides for direct communications, uploading and downloading of programs or data, and recharging.

Other vaporization means may be provided, such as a heat source (burner, flame, electrical). Temperature may be controlled in the manner of other parameters discussed herein. In yet another embodiment, a unit has multiple vaporization elements, and can vaporize different substances from multiple refillable chambers or multiple ampoules simultaneously, in sequence, or some combination thereof.

Figure 25:
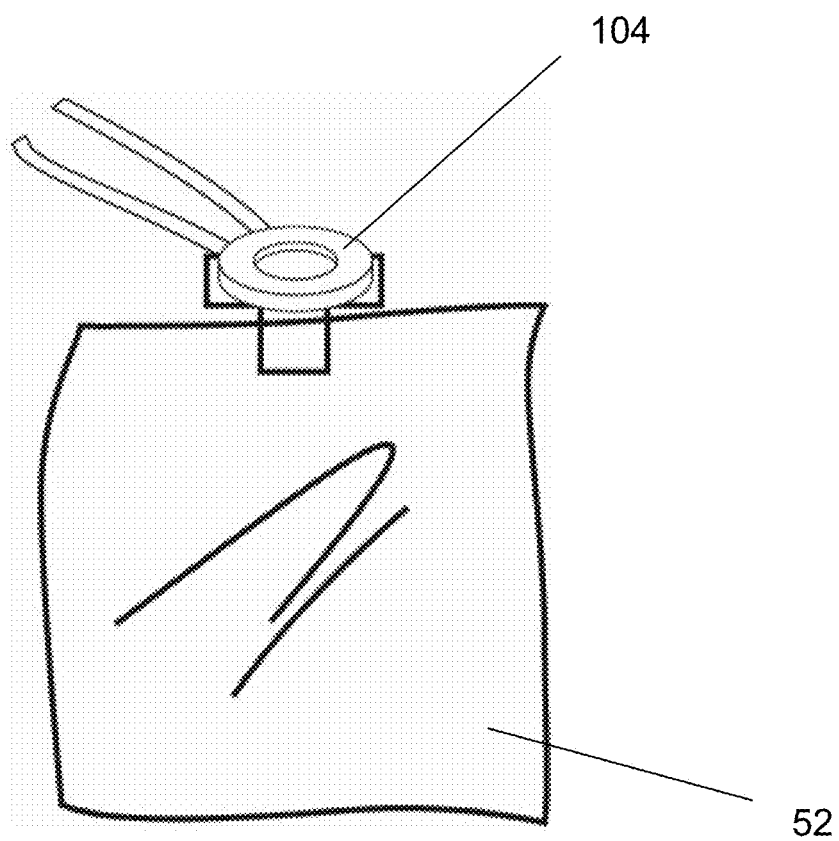
FIG. 25 shows a view of an ampoule in pouch form with a piezoelectric unit in a top position.
Figure 26:
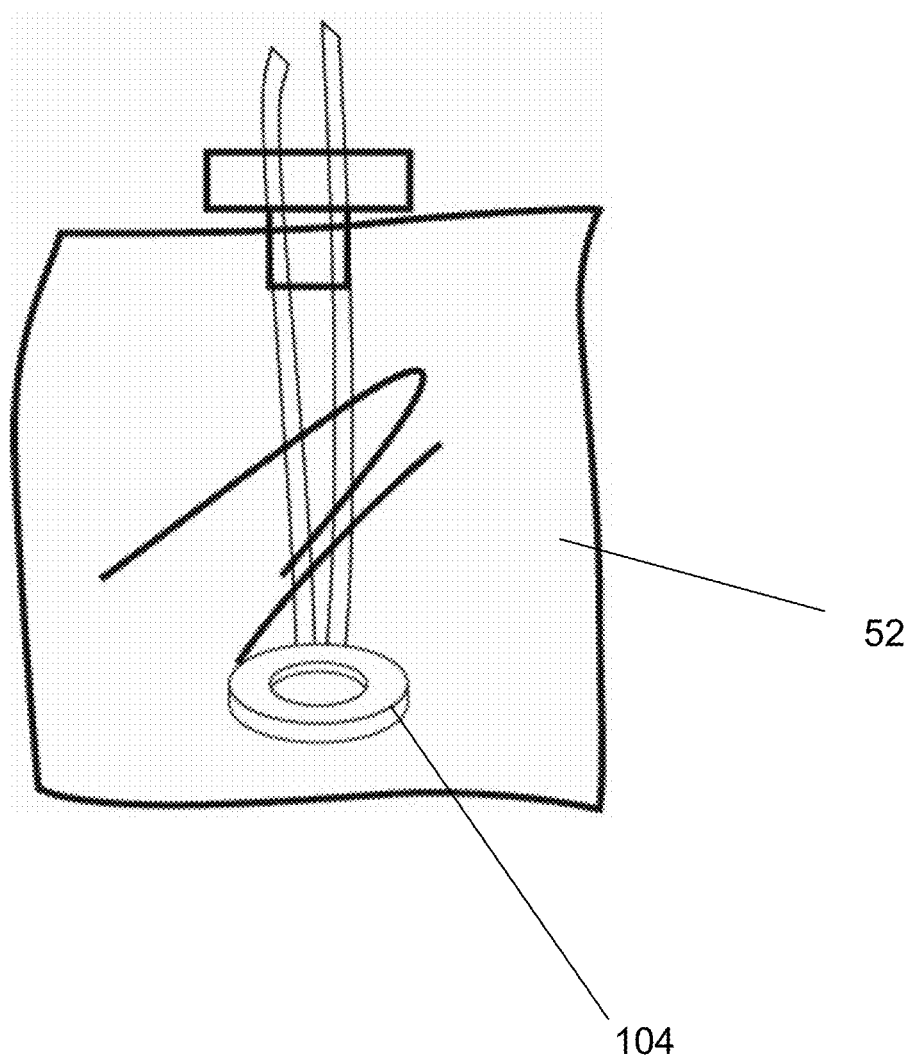
FIG. 26 shows a view of an ampoule in pouch form with a piezoelectric unit in a bottom position.
Figure 27:
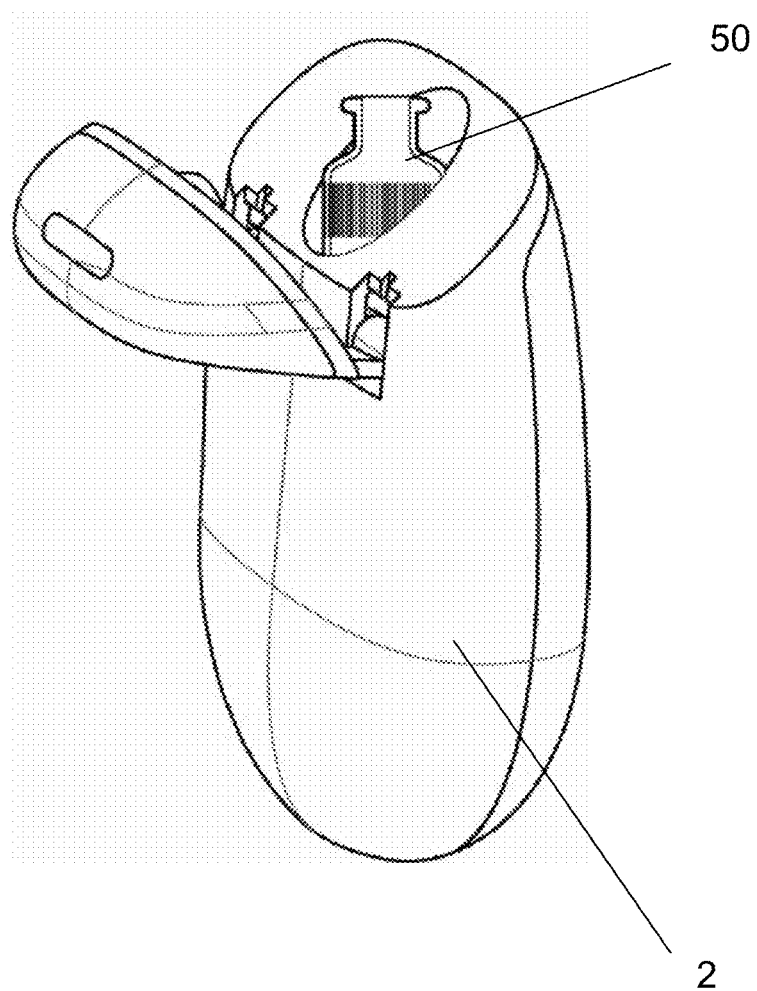
FIG. 27 shows a view of an ampoule inserted into a personal vaporizing unit.

In several embodiments, the ampoule 50 itself may comprise a piezoelectric unit 104, and may be multiple use or single use. The ampoule may be hermetically sealed, and made of any suitable material, including, but not limited to, glass, plastic, polymer, metal, or the like. The ampoule may be rigid, or flexible (e.g., a flexible pouch 52, as seen in FIGS. 25-26). In one embodiment, as seen in FIGS. 12-16 the ampoule comprises a barrel shape with a proximal end and distal end, the proximal end being open and extending into a rim or two opposing tabs perpendicular to the axis of the barrel, each tab comprising an ergonomic and/or flat radius section following the extension point of the tab.

The piezoelectric unit 104 may be located in the top of the ampoule, such as in a cap that screws onto or is otherwise attached to the body of the ampoule. The cap may be permanently affixed to the ampoule, such as by welding, gluing, or adhesive, or may be removable. The piezoelectric unit may be held in an insert or holder used to position the piezoelectric unit directly over the opening of the ampoule, thereby providing consistent flow of the material. The piezoelectric unit may be in the form of a wafer or similar configuration. Power may be supplied to the unit by guide wires or connections to a power source in an inhaler unit in which the ampoule is inserted, or by a battery or similar power source attached to or embedded in the ampoule.

Once the piezoelectric unit is removed, or the cap is opened, the integrity of the electronics is destroyed (e.g., the guide wires are broken or torn) to prevent re-use (i.e., the unit can only be used once with the pre-loaded material, and must be discarded after use). This safeguards against the use of illegal drugs, improper medicaments, or the like.

In additional embodiments, the piezoelectric unit may embedded into the side or bottom of the body of the ampoule in middle or bottom positions. The piezoelectric unit may be inaccessible, ensuring that the ampoule is used only once and cannot be refilled.

Figure 20:
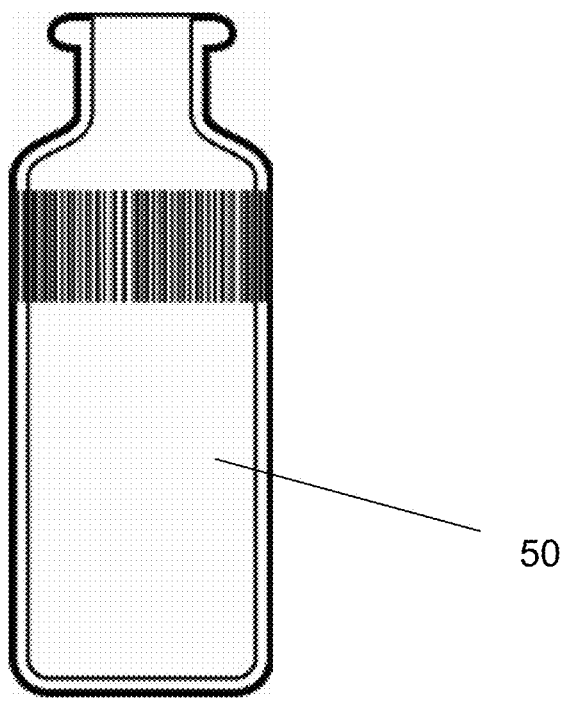
FIG. 20 shows a view of an ampoule with bar code.
Figure 21:
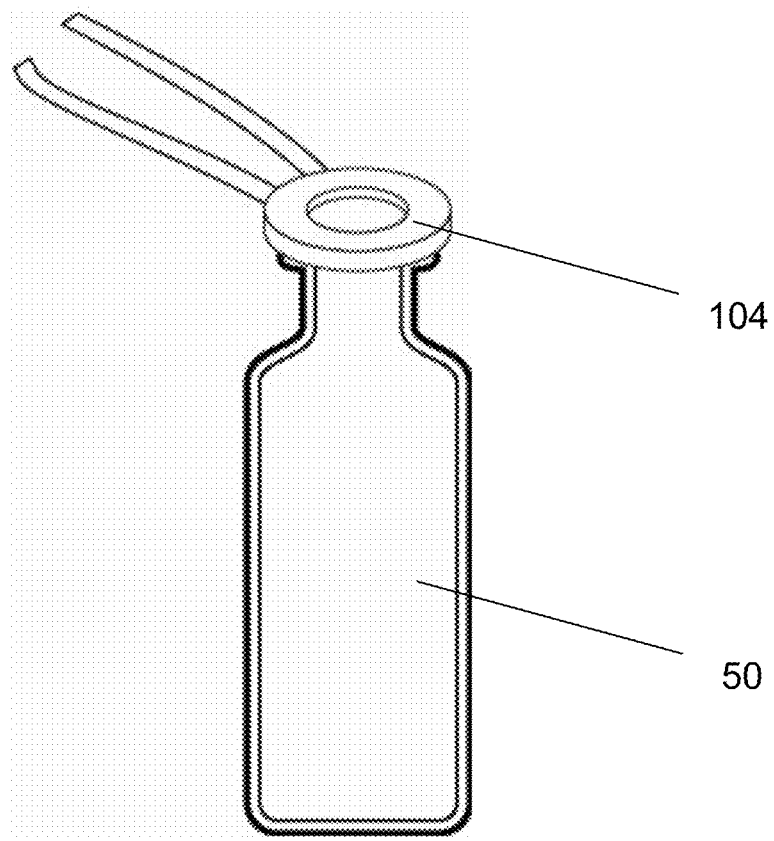
FIG. 21 shows a view of an ampoule with a piezoelectric unit in a top position.
Figure 22:
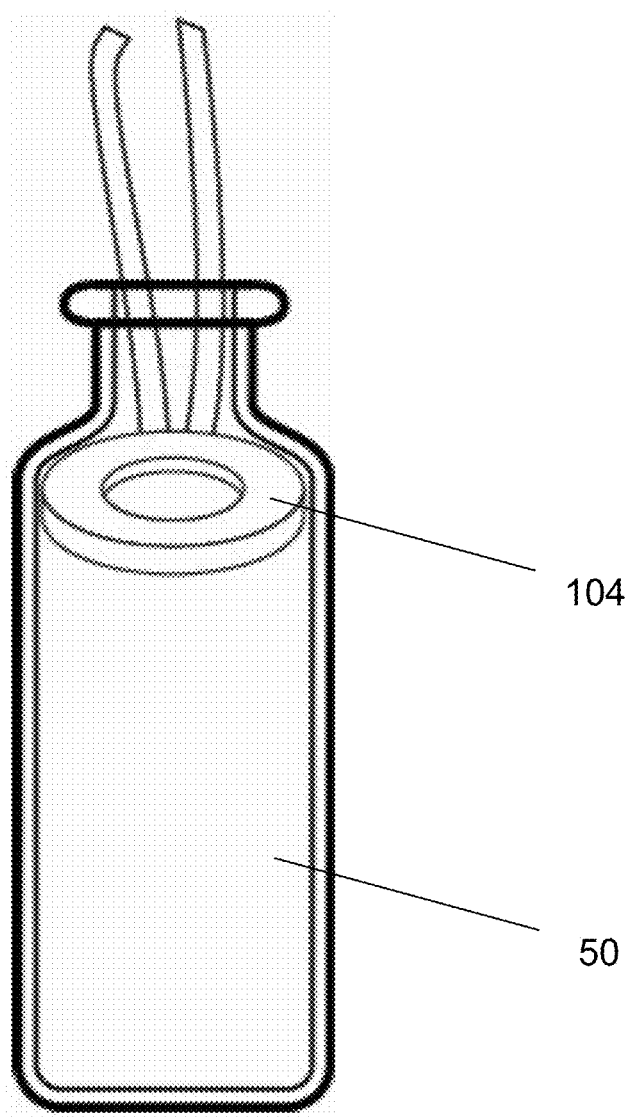
FIG. 22 shows a view of an ampoule with a piezoelectric unit in a middle position.
Figure 23:
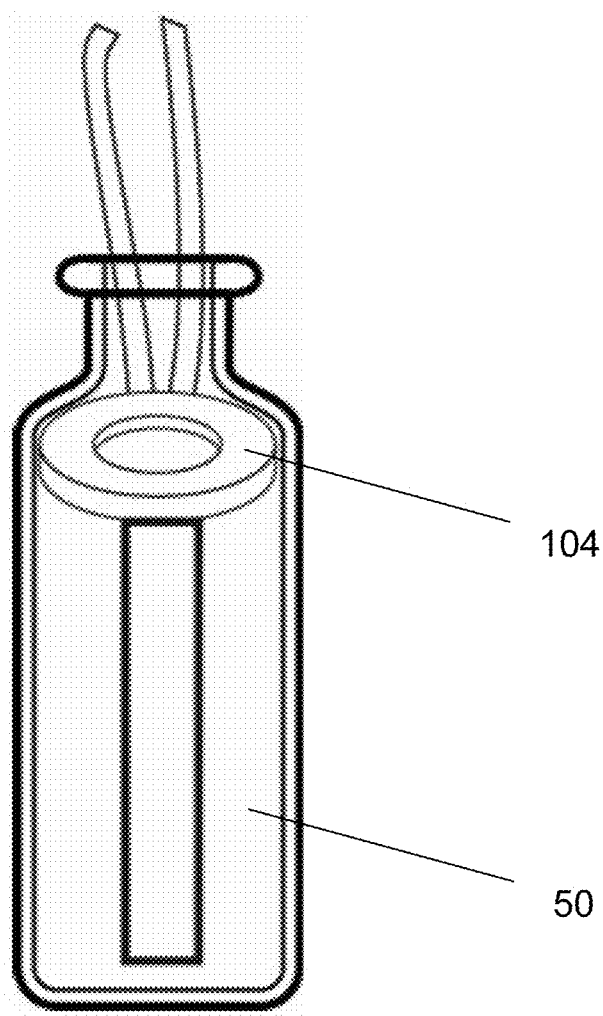
FIG. 23 shows another view of an ampoule with a piezoelectric unit in a middle position.
Figure 24:
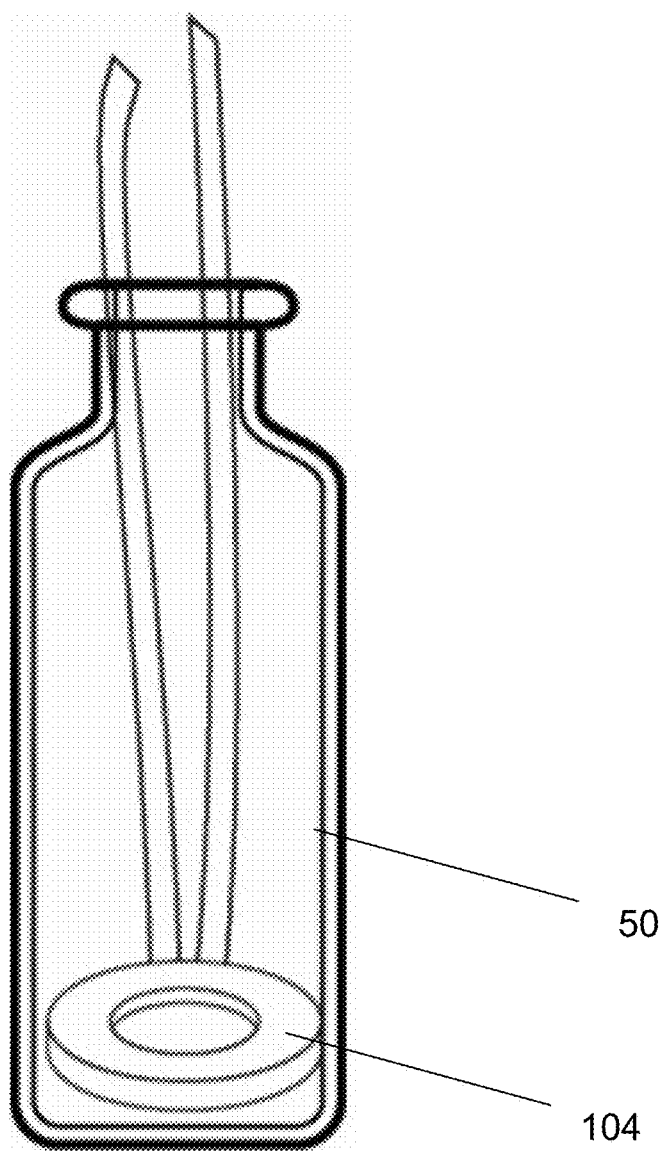
FIG. 24 shows a view of an ampoule with a piezoelectric unit in a bottom position.

The exterior of the ampoule may be printed directly onto with a description of the contents, a bar or similar code, as seen in FIG. 20, and other information.

In yet a further embodiment, the unit has a computer memory storage capability, and stores vaporization treatment data so that the details of the vaporization treatment, such as, but not limited to, the substance, amount of substance vaporized (i.e., dose), the time of the application, the length of time for the vaporization, and similar data. The vaporization treatment data can be recorded and stored in real time, and transmitted in real time or at a later time to a health or wellness program or similar applications, and used to evaluate clinical or medical treatment compliance and effectiveness. The information may be transmitted or downloaded by wired or wireless connection 132, 134 as described above. The unit may have one or more means of wireless communication (e.g., wireless chip, Bluetooth), and wired communication (e.g., data ports, USB ports).

The atomization chamber 100, conduit 120, transducers or atomizers 102, or other components of the device, may be cleaned between uses using a cleaning solution, by one or more interior UV (ultraviolet) light or radiation sources 210 along the chamber and conduit, or combinations thereof. UV light/radiation kills cells by damaging cell DNA.

The device also may divide the main body into an upper portion 150 and lower portion 152, hingedly attached 154. The ampoule 50 may be inserted into the lower portion when the device is opened (the ampoule may be centered or off-centered). When closed, the ampoule is connected to the piezoelectric transducers or atomizers 102 and atomization chamber 100, which are located in the upper portion.

In yet another embodiment, one or more light sources 200 (such as, but not limited to, light-emitting diodes (LEDs), laser diodes, fiber optics, full spectrum light sources, RGB LEDs, and the like), vibrational sources (ultrasonic or otherwise), heating sources or elements, piezo transducers, or combinations thereof (collectively, "therapy elements"), may be located on or in the mouthpiece unit, or a portion of the device insertable into the mouth, to provide light-related or other therapy to the mouth, lips and gums. The device can comprise a number of individual light sources. The configuration or patterns of light sources can vary, as well as the color and intensities (i.e., milliwatts ranges) of the light sources. Likewise, the light sources can comprise various mixes of types of light sources. Different colors and intensities may be used for different treatments. In addition, different colors and intensities may be used in different areas.

Physicists have recognized light to be a pure form of energy that is a part of the electromagnetic radiation spectrum. Within this spectrum, the various colors of light each represent unique wavelengths and frequencies that produce therapeutic effects when absorbed through the interior of the mouth. Visible red light tends to stimulate growth at the cellular level whereas blue light has more of a soothing affect. The application of low-level light therapy on the body or areas of the mouth produces a photochemical reaction in the cell. During this process, photons of light are absorbed into the treated cell to increase and stimulate stored energy. As a result, this stored energy transforms into chemical energy that can be used to regulate cellular activity; including enhanced ATP synthesis, protein synthesis, cellular proliferation, and growth factor secretion. Low-level light therapy thus increases energy, reduces pain and inflammation, and reduces stress.

The light sources emit energy in the form of photons when switched on, delivering energy to the interior of the mouth, and penetrating the layers of mouth to produce a non-thermal photochemical effect at the cellular level. The therapy is noninvasive, and avoids the potential side effects of older forms of therapy, such as drug therapy.

Different arrangements (e.g., colors, intensity, locations) of light sources and other therapy elements may be provided on different mouthpiece units or other attachments, which can be interchanged as desired. The present invention in several embodiments thus comprises a phototherapy device with a plurality of light sources arrayed on an interior-facing of the mouth. Various circuit boards contain various orientations, configurations or patterns of light sources, in a variety of colors and intensities (e.g., milliwatts range). Examples of light source orientation include, but are not limited to, a fixed straight position, a variety of angled positions (i.e., angled with respect to the circuit board) allowing bi-directional ability of light to crisscross, or combinations thereof.

Different colors may be used for different treatments. In several embodiments, RGB LEDs are used. RGB LEDs are red, blue and green LEDs that combine these three colors to produce over 16 million hues of light. Not all colors are possible, as some colors are"outside" the color triangle formed by the RGB LEDs. Further, pigment colors such as brown or pink are difficult, or impossible, to achieve. In several embodiments, RGB technology utilizes the color mixing properties of red, green, and blue LED chips that are provided on a reflector. A photo mixing material and filler resin scatters the light rays to uniformly combine the rays emitted from the LED chips. The photo mixing material and filler resin are applied onto upper sides of the light emitting diode chips while being mixed with each other, and the photo mixing material is uniformly dispersed in the filler resin.

In several embodiments, the light sources include red, blue, green and orange colors. These colors have the following effects:

Red: stimulates vitality and growth; good for fatigue and debilitating conditions; use for deficient nutrition, dormant conditions, poor appetite, constipation, depression, drowsiness, and paralysis.

Blue: slows down growth; calming; acts as a sedative; relieves excitement and inflammation; resets "biological clock" of the human body using doses of 20 minutes; blue light to Alzheimer's patients helped biological clock to sleep longer at night; use for nervousness, irritability, fussiness, feverishness; apply to all conditions where inflammation is present; use for internal bleeding, nervous conditions.

Green: slows down growth; calming; relieves excitement and inflammation; useful when combined with blue/red and yellow as a brain/nerve stimulate and laxative.

Orange: a combination of red and yellow is powerful in colds and sluggish/chronic conditions as it helps release stored energy.

The device also may contain optical fibers, or optical fiber containing extending units or arms, to carry light to the interior of the mouth or throat. Light sources may be placed in a variety of configurations or patterns, in a similar manner as described above, to allow light to impact the inner mouth and brain, or to illuminate the area inside of the mouth. Removable faceplates may also be used with the ULiv device.

The light sources can be controlled by wireless (Wi-Fi or Li-Fi) or wired connection through a control unit, or a control program or application on a computing device, mobile or portable computing device, touchpad or tablet device, cellphone, or the like. LiFi is Light Fidelity, a bidirectional, high speed and fully networked visible light wireless communication technology similar to Wi-Fi. The user can control color, type, duration, wavelength amplitude, wavelength phase, and frequency (pulse) of the light sources, and similar characteristics of the therapy elements in general, being activated during therapeutic application, as described in further detail herein. The operator can select the frequency (pulse), wavelength, amplitude, and wave type associated with each light-emitting source. This phase relationship allows for each channel to be specifically programmed with frequency and peak-to-peak amplitude allowing multiple channels to operate at a different frequency (pulse) and amplitude. Thus, the phototherapy device can produce multiple wavelengths, multiple wave types, multiple frequencies (pulses), and multiple amplitudes.

In several embodiments, the device can provide any light frequency within the pulsing range of 0 Hz to 100,000,000,000 Hz, and can run all safe wavelengths of the electromagnetic spectrum, including visible light and near-infrared light. In several exemplary embodiments, the power output per light source ranges from 1 mW to 300 mW.

In several further embodiments, the present invention incorporates the geometric configuration of single light technology or multiple light technologies, wavelength, amplitude and power output, referred to as the array. The geometric configuration is not limited to any single configuration and can include any geometric configuration of wavelengths, power output, amplitude, and wave types. The array is engineered to produce multiple wavelengths, power outputs, amplitudes and wave types producing therapeutic benefits to human brain and mouth area. This is accomplished by utilizing expandable software, smart chips, adaptive lenses, and light producing technology that is completely scalable and configurable to operator needs. The geometric arrangement of the light technology is not limited to any single geometric configuration, wavelength, power output, amplitude, or wave type. The array can be configured to support any geometric configuration of multiple wavelengths, multiple power outputs, multiple amplitudes, or multiple wave types.

In several embodiments, the present invention will only work with specific control boxes, accessories, or computing devices, which can be self-identifying through "handshake" communications technology. Utilizing handshake technology will only pair specific units to specific accessories. A specific circuit board chip may be utilized in each and every piece of equipment. This can also be controlled through a phone app which will only allow the ULiv to hookup to a specific code within the program of the app. These chips include a one-of-a-kind code that forms a unique link to each other. The circuit board may be a variable frequency circuit board. Specific RF chips may be installed in each and every unit so that identifications can be placed into each piece of equipment to identify purchase dates and other necessary information.

In yet a further embodiment, the invention is equipped with an USB port and wireless circuit board that will operate and control peripheral devices by the digital interface of the device. Peripheral devices include, but are not limited to, light technology devices and any device that generates frequency or electrical pulse. The peripheral devices may be activated upon a passcode entered into a digital interface of the device.

Figure 17:
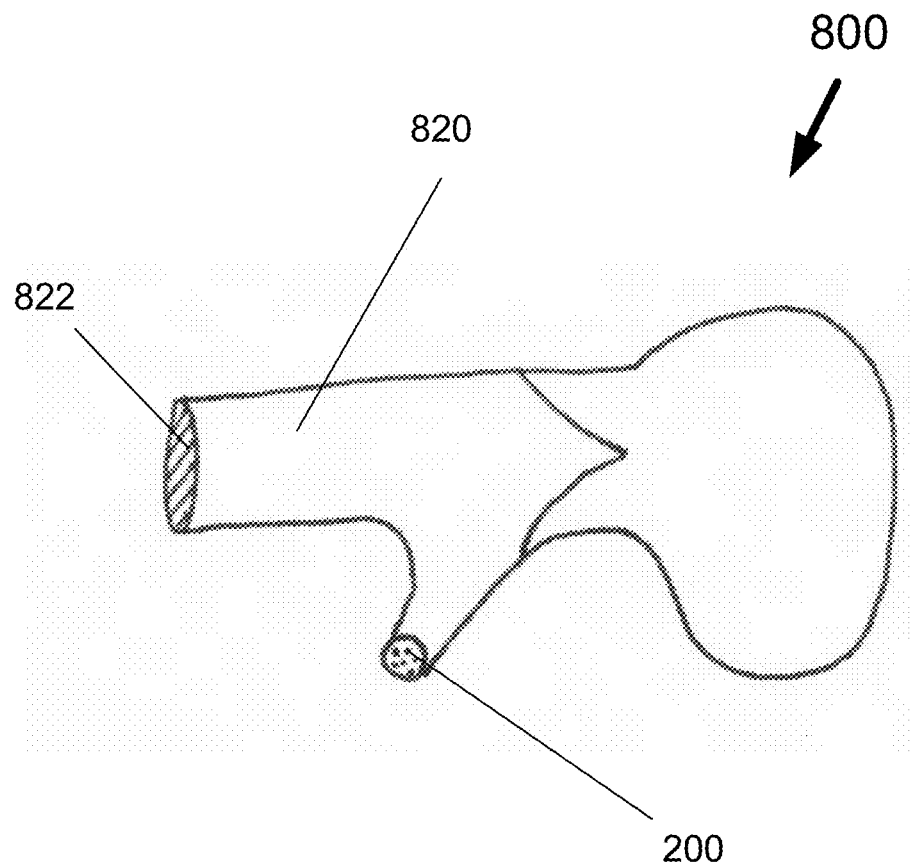
FIG. 17 shows a side view of a hand-held analysis device.
Figure 18:
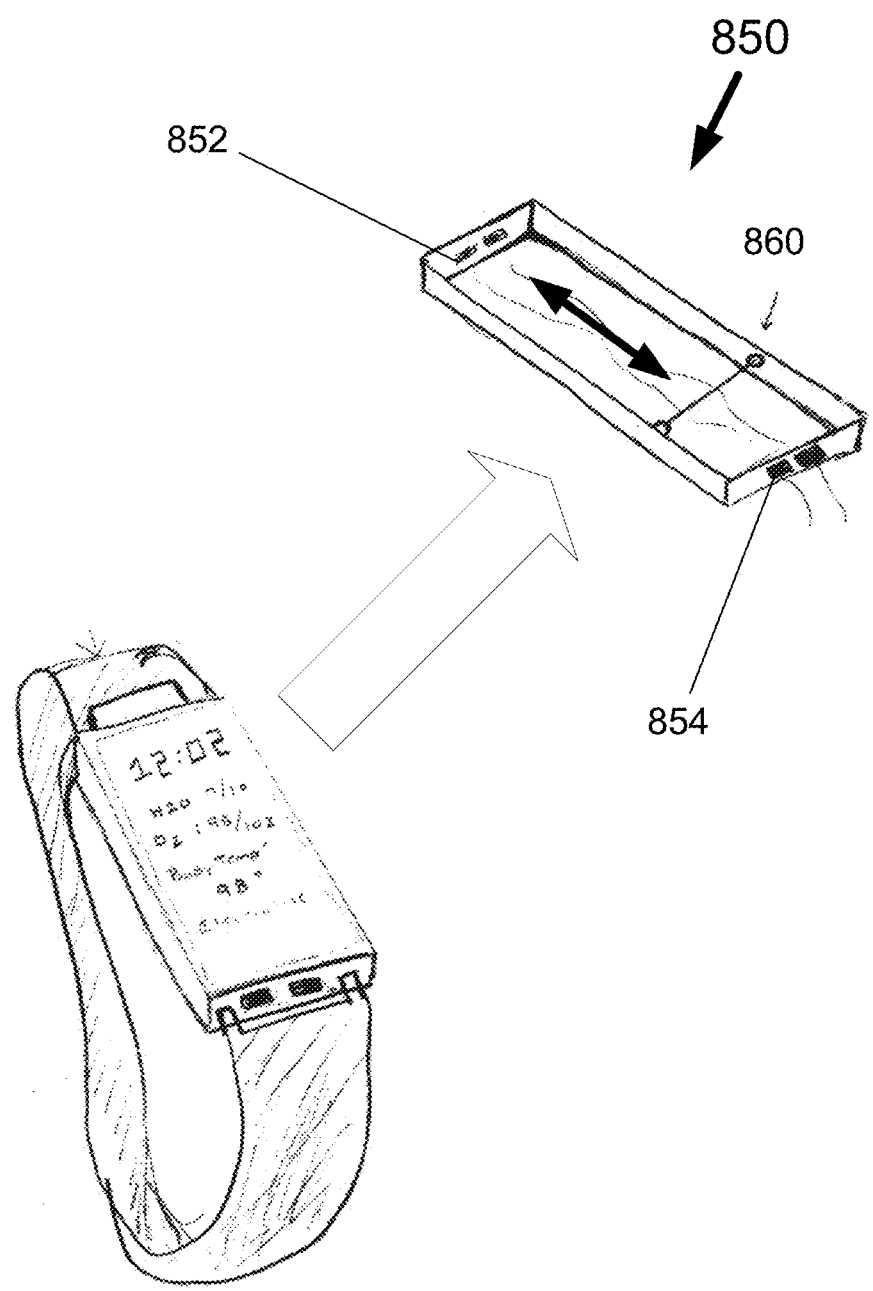
FIG. 18 shows views of a wearable analysis device.
Figure 19:
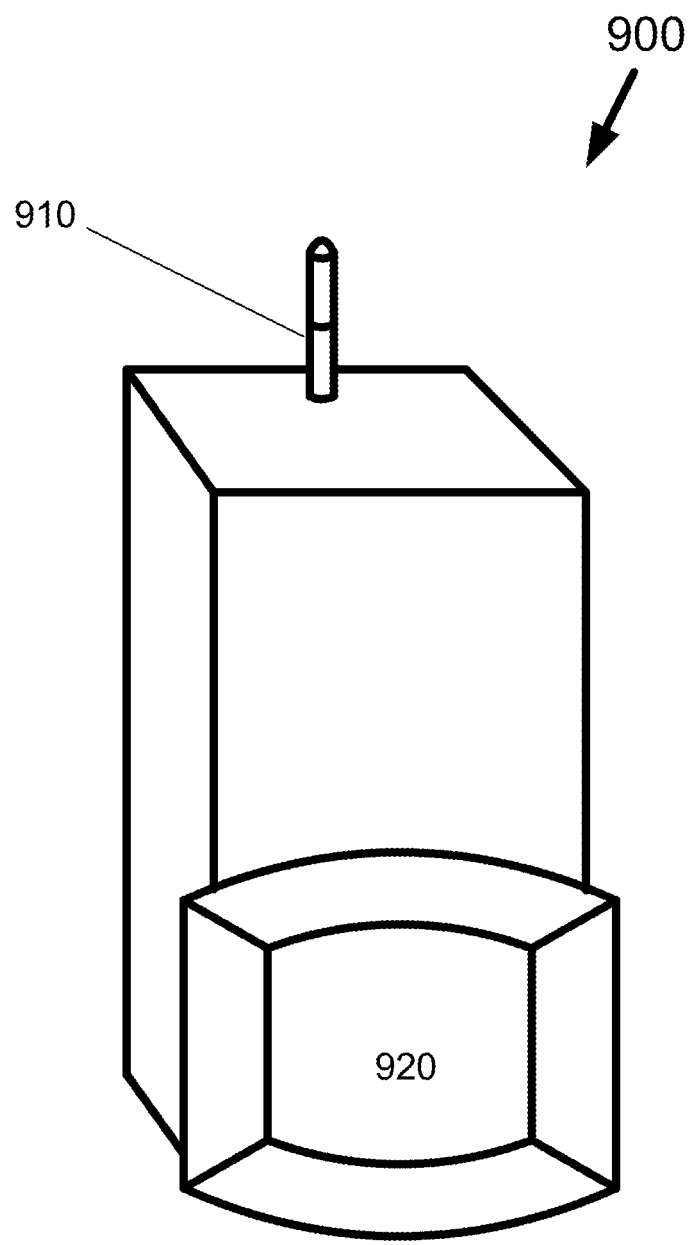
FIG. 19 shows a front view of a analysis device adapted to be plugged into a mobile computing device.

A breath analysis device may be used independently, or in conjunction with the personal nebulizer or vaporizing unit device described above. In several embodiments, as seen in FIGS. 17-19, the breath analysis device comprises a handheld or wearable device 800 with an exhale feature to capture and read the content of exhaled air. In one embodiment, the held-device comprises a mouthpiece 820 with a mouth port 822 for insertion into the user's mouth. The mouthpiece may be made of rubber or similar material, and may be detachable from the main body. One or more light sources 200 may be placed on the mouthpiece or extensions thereof for light therapy treatment, as described herein.

In another embodiment, the breath analysis device comprises a analysis unit 850 mounted as a wearable on a band. The top surface of the unit may comprise a display providing time and other information. One end of the unit comprises a mouth port 852 with an intake port 854 at the opposite end. The interior of the unit comprises a spectrographic laser 860 for analysis of the breath passing through the unit.

In yet another embodiment, the analysis device comprises an analysis attachment unit 900 with a mouthpiece 920 and a plug 910 suitable for connection with a mobile computing device, which can be used as a display, recording and control unit for the attachment unit.

The analysis device comprises a valving system, a vent tube, and one or more detectors. The valving system comprises three ports to manage air flow powered by a user's inhaling and exhaling. The user places the mouth port into his or her mouth, and inhales and exhales through/into the mouth port. During inhalation, an intake port allows air to flow into the device and through the mouth port into the body of the user. During exhalation, air flow into the device through the mouth port, and through a third port into a detection/vent tube or chamber.

In one embodiment, the detection/vent tube is a flexible tube made of plastic or similar material that rigidly maintains radial integrity. At least one transducer is located along the walls of the tube in at least one receiving port. Receiving ports allow one end of a transducer to be exposed to the air stream inside tube, and allow electrical connections to a detection process in the device. Transducers may include capnography devices, temperature transducers, water vapor transducers, blood alcohol transducers, airflow transducers, and pH transducers. Transducers may be placed at either or both ends of the valving system to measure input and output values for the above, and other parameters, such as pressure. Transducers also may be used to detect the presence or concentration of one or more of the therapeutic substances provided by the personal nebulizer or vaporizing unit, as described above.

The system of the present invention includes a computer-implemented program or programs to carry out various functions described herein. The program or programs may be installed on and operated through an Internet website (e.g., through a web browser), as a client program on a computer or computer network, as an application on a mobile computing device, or combinations thereof. As described above, one or more personal nebulizer or vaporizing devices and personal breath analysis devices may comprise one or more processors or microprocessors, digital or computer storage memory and devices, and communications means. Communications means include, but are not limited to, a wireless or Bluetooth or BLE chip for wireless communications, or a USB, mini-USB, or similar communications port for direct wired communications. Communications includes uploading and downloading of programs or data to and from the devices. Calibration and control of the operation of each device may be controlled by the user manually using a control on the unit, automatically controlled by the processor or microprocessor, automatically controlled, based upon a code or symbol (e.g., bar code) on an ampoule or other component, or remotely controlled, such as by wireless connection to a computer or mobile device. For example, the computer memory storage of a vaporization devices stores vaporization treatment data so that the details of the vaporization treatment, such as, but not limited to, the substance, amount of substance vaporized (i.e., dose), the time of the application, the length of time for the vaporization, and similar data, can be recorded and stored in real time, and transmitted in real time or at a later time to the system of the present invention, or a similar health or wellness program or similar applications, and used to evaluate clinical or medical treatment compliance and effectiveness.

A breath analysis device may be used independently, or in conjunction with the personal nebulizer or vaporizing unit device described above. In several embodiments, the breath analysis device comprises a hand-held device with an exhale feature to capture and read the content of exhaled air. The breath analysis devices comprises one or more transducers that are exposed to the exhaled air in the device, and allow electrical connections to a detection process in the device. Transducers may include capnography devices, temperature transducers, water vapor transducers, blood alcohol transducers, airflow transducers, and pH transducers. Transducers may be placed at intake and outflow ends of the breath analysis device to measure input and output values for the above, and other parameters, such as pressure. Transducers also may be used to detect the presence or concentration of one or more of the therapeutic substances provided by the personal nebulizer or vaporizing unit, as described above.

Figure 28:
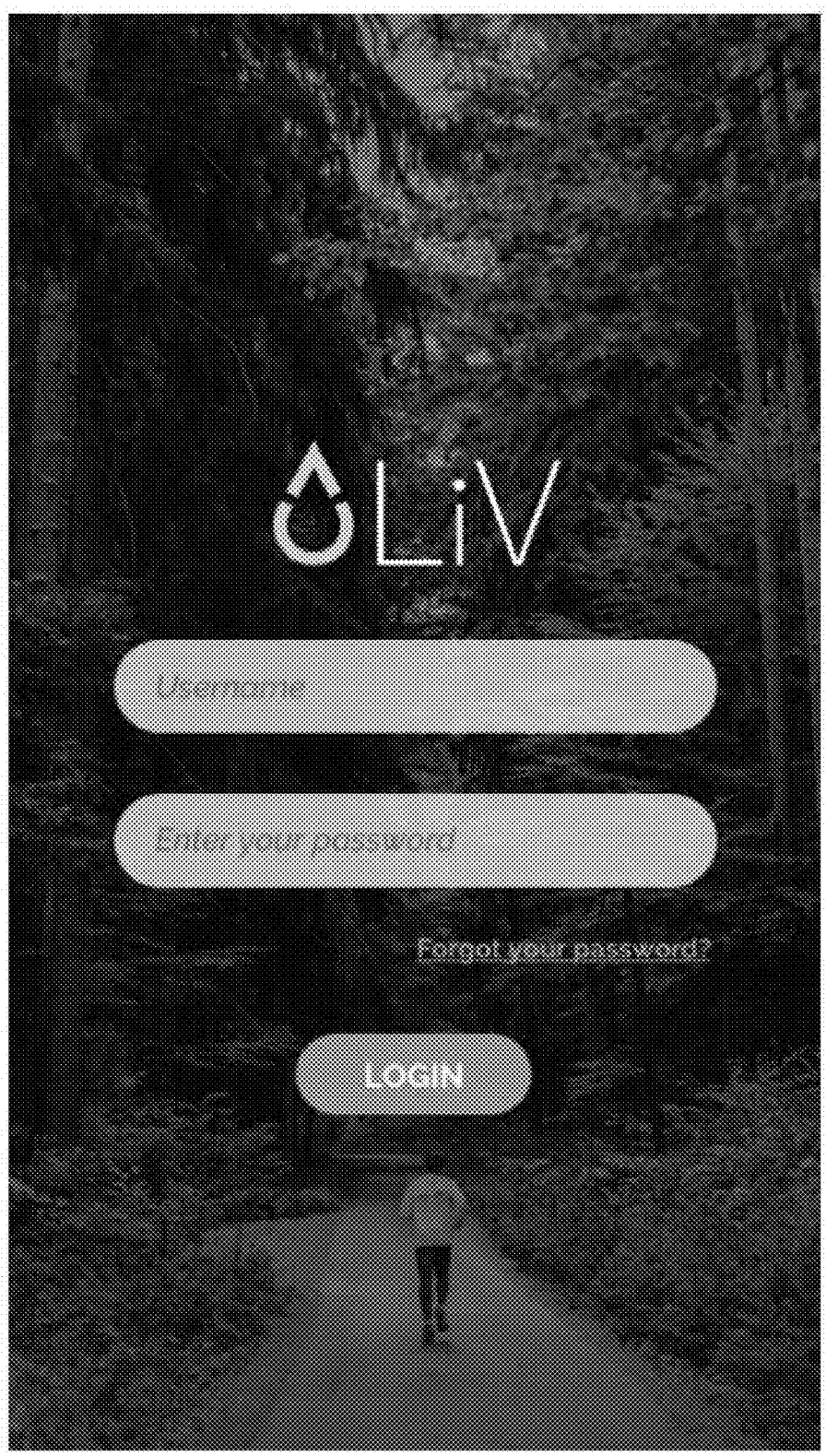
FIGS. 28-39 show views of a graphic user interface of a system application in accordance with an embodiment of the present invention.
Figure 29:
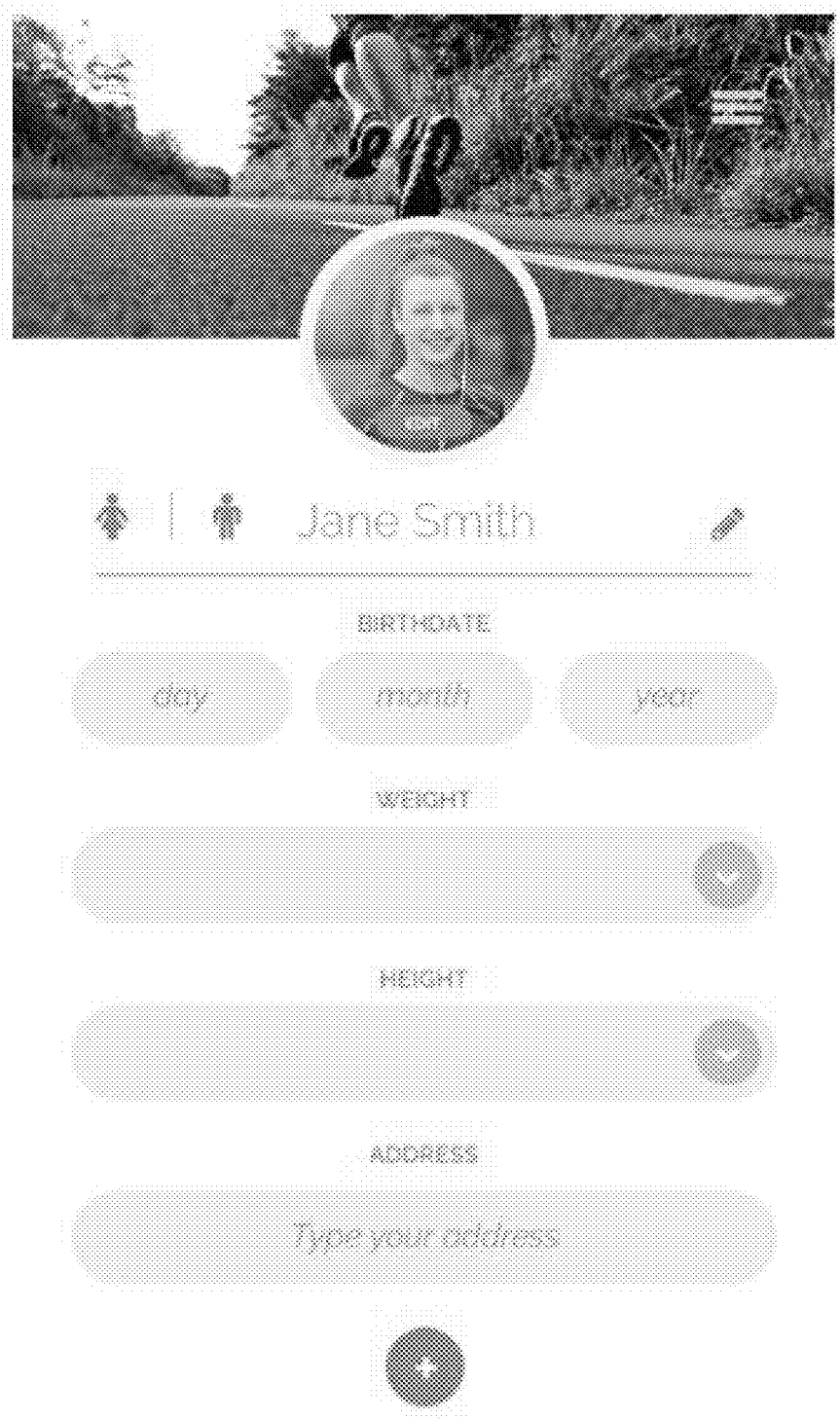
Figure 30:
Figure 31:
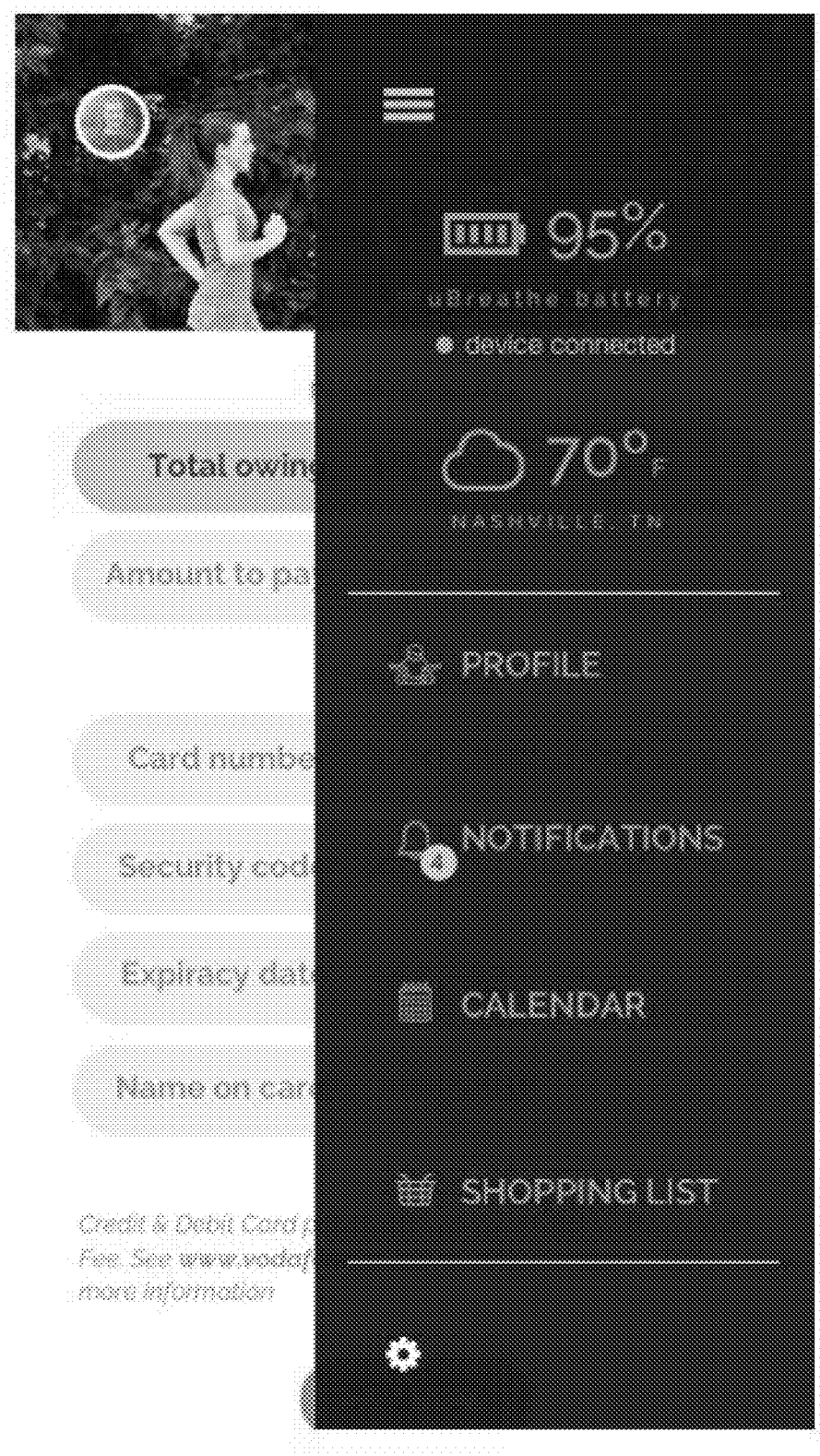
Figure 32:
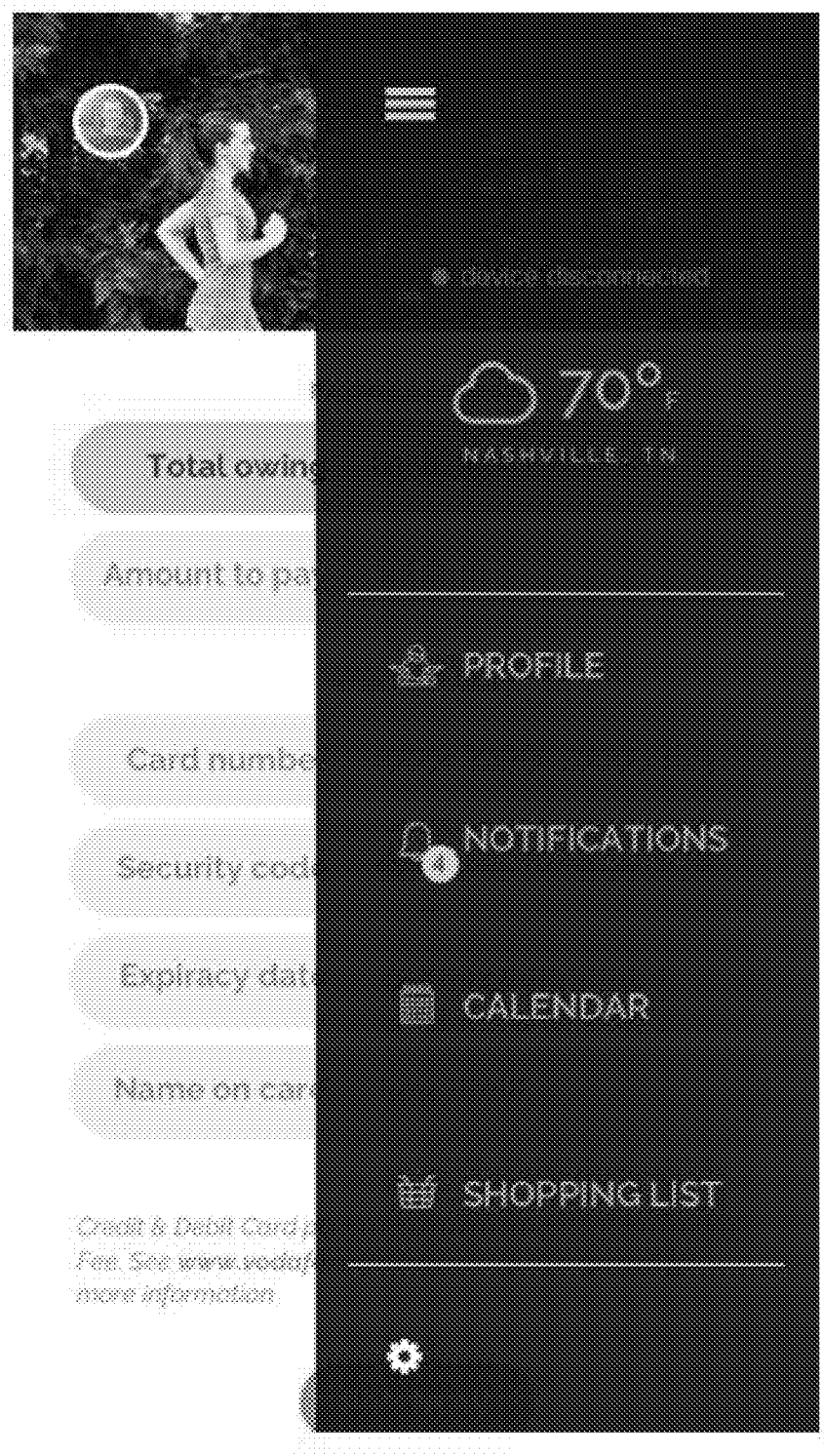

FIGS. 28-39 show examples of various user interface screens from a computer-based application on a mobile computing device for managing the components of the system of the present invention, and to carry out various functions described herein. FIG. 28 shows an exemplary login screen for an application on a mobile computing device (e.g., cell phone, smart phone, or tablet computing device). After logging in for the first time, the user is prompted to enter basic identification information, as seen in FIG. 29, and financial payment information, as seen in FIG. 30. FIGS. 31 and 32 show examples of a basic interface menu including a connection status indicator and device battery level for a personal inhalation device that is connected with the system. This basic interface menu can be called up over most interface screens of the system.

Figure 33:
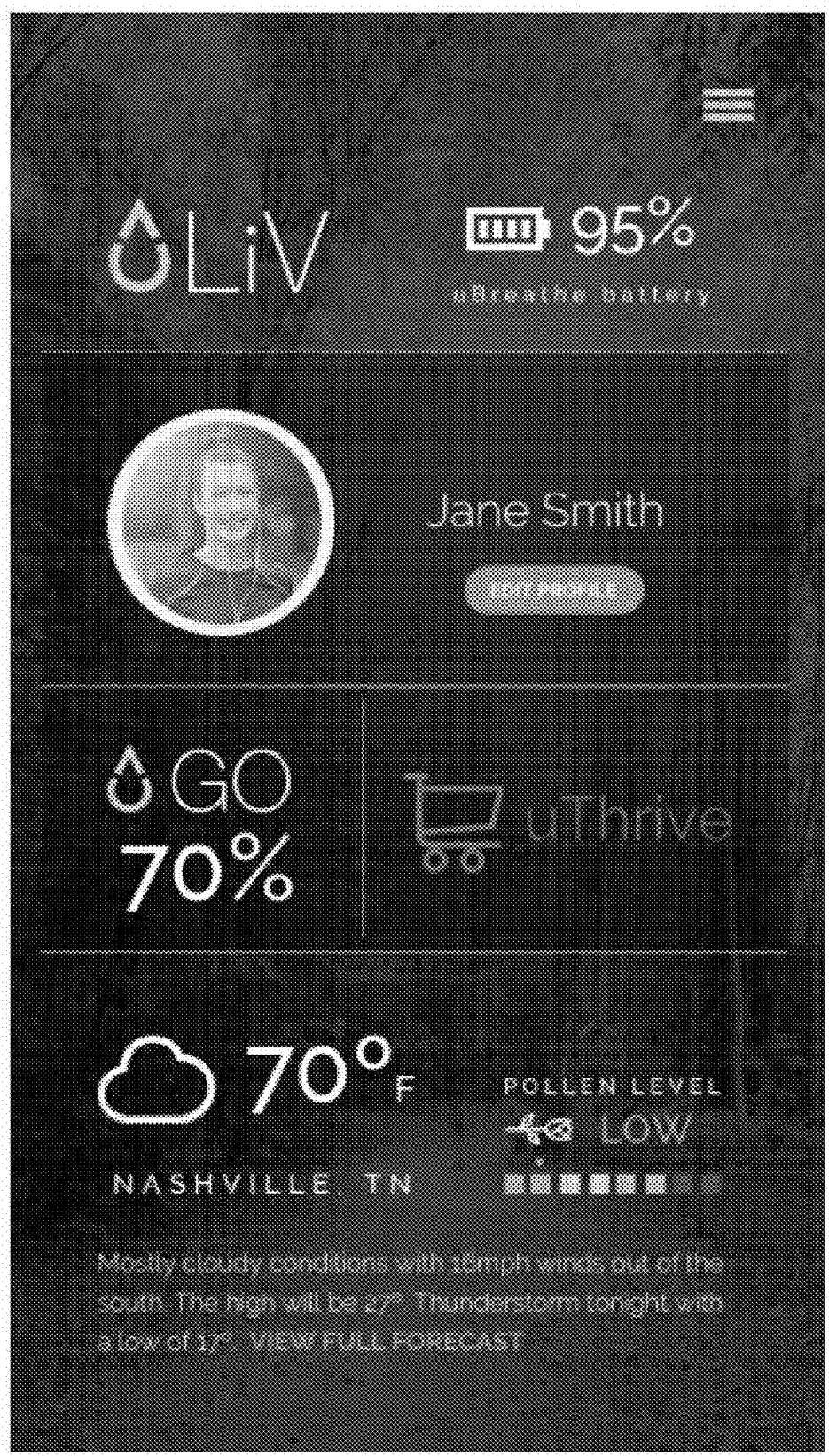
Figure 34:
Figure 34:
Figure 34:
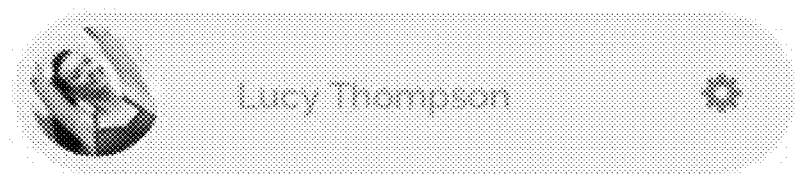
Figure 34:
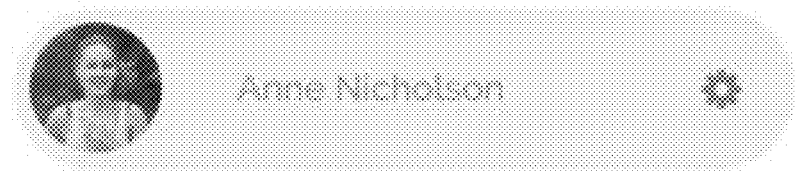
Figure 34:
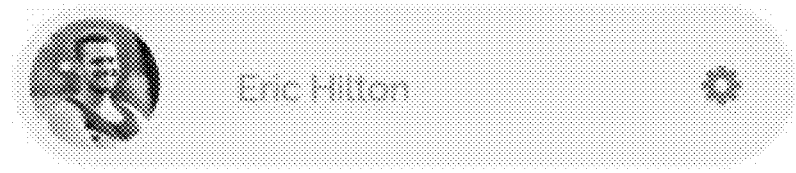
Figure 34:
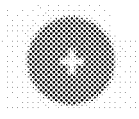

FIG. 33 shows an example of a basic information page for the user. A user also may access a list of other users, or friends using the system, as seen in FIG. 34. Users can opt to be include in a network of friends or users, or be anonymous in the system.

Figure 35:
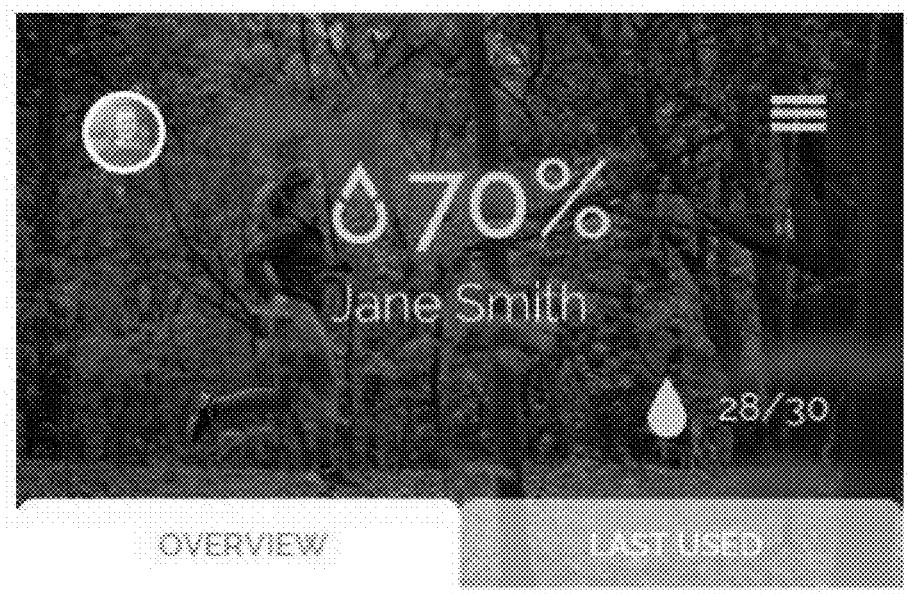
Figure 35:
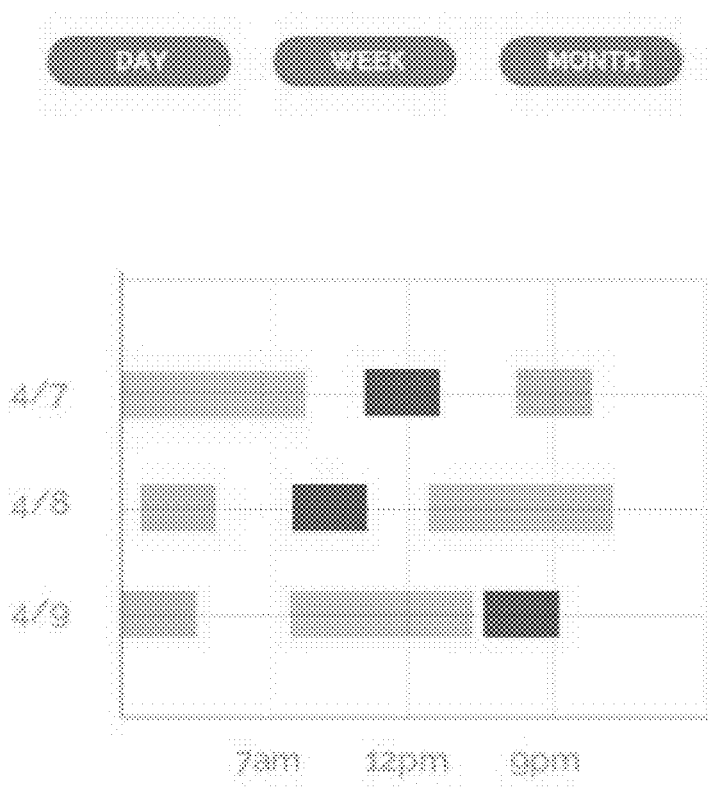
Figure 36:
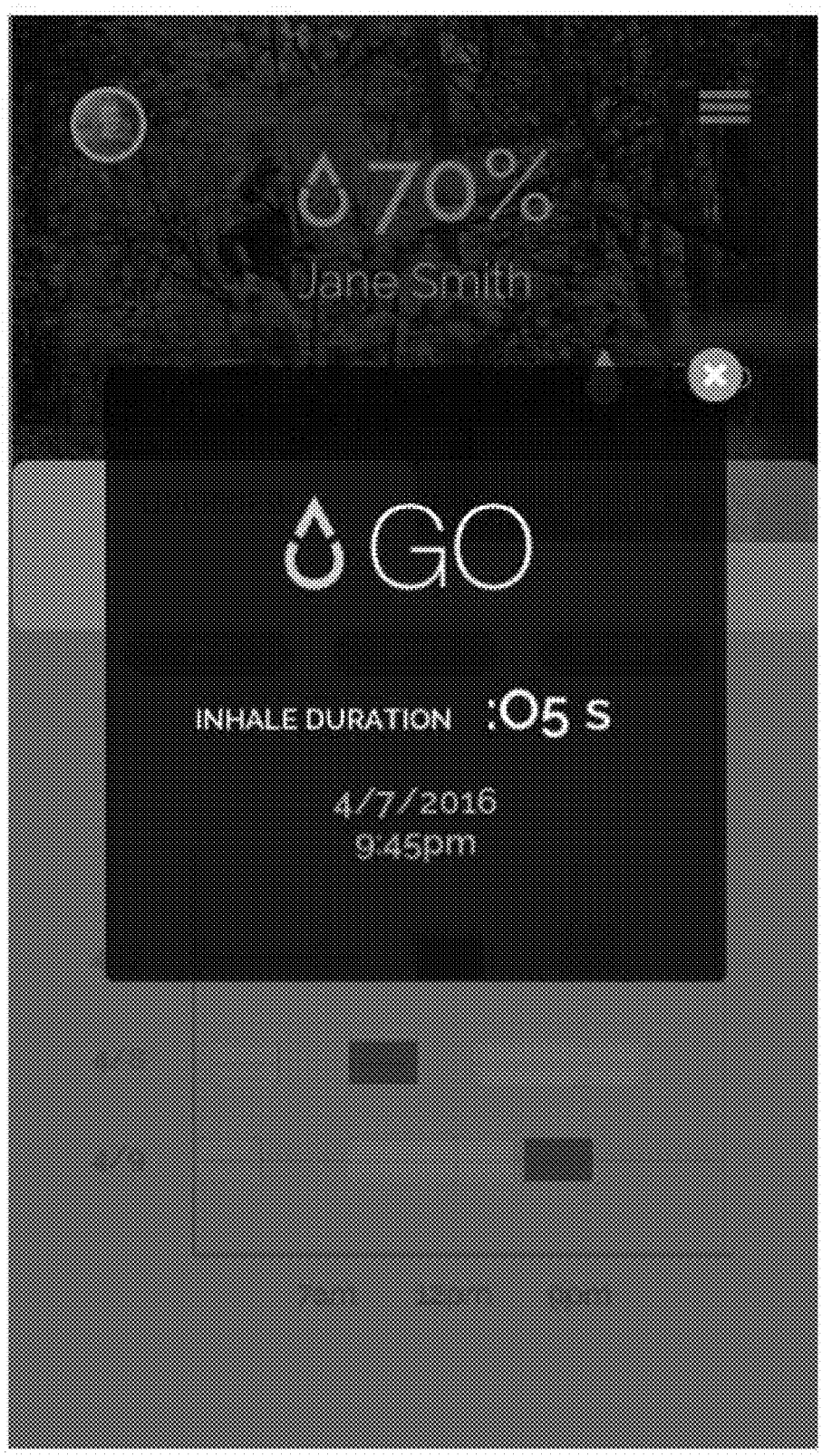
Figure 37:
Figure 37:
Figure 37:
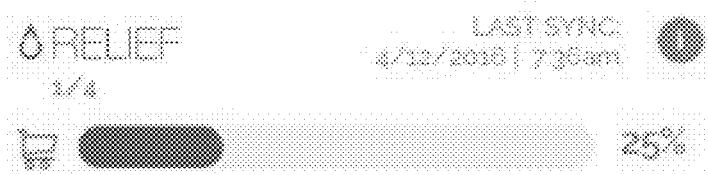
Figure 37:
Figure 38:
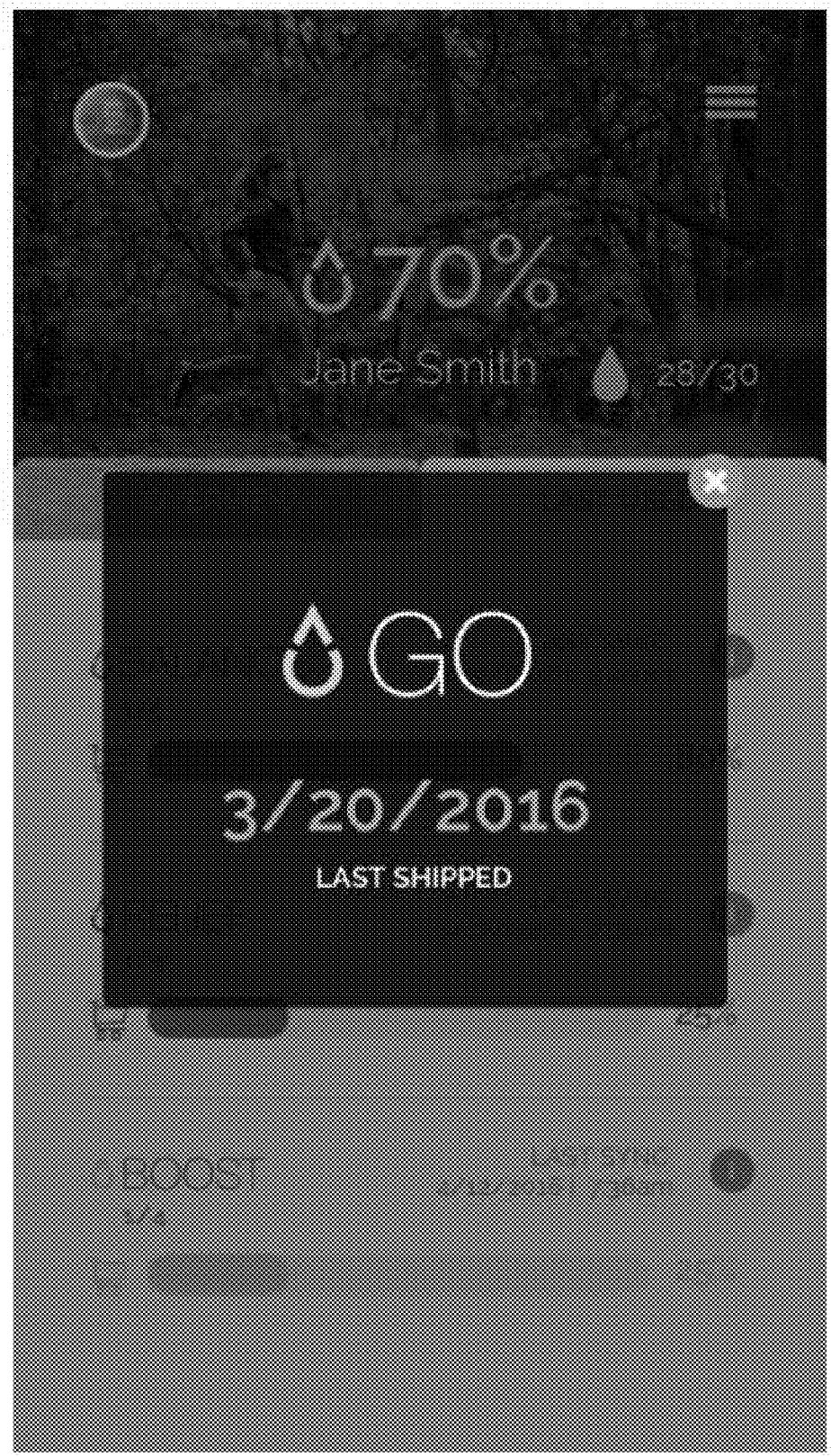
Figure 39:
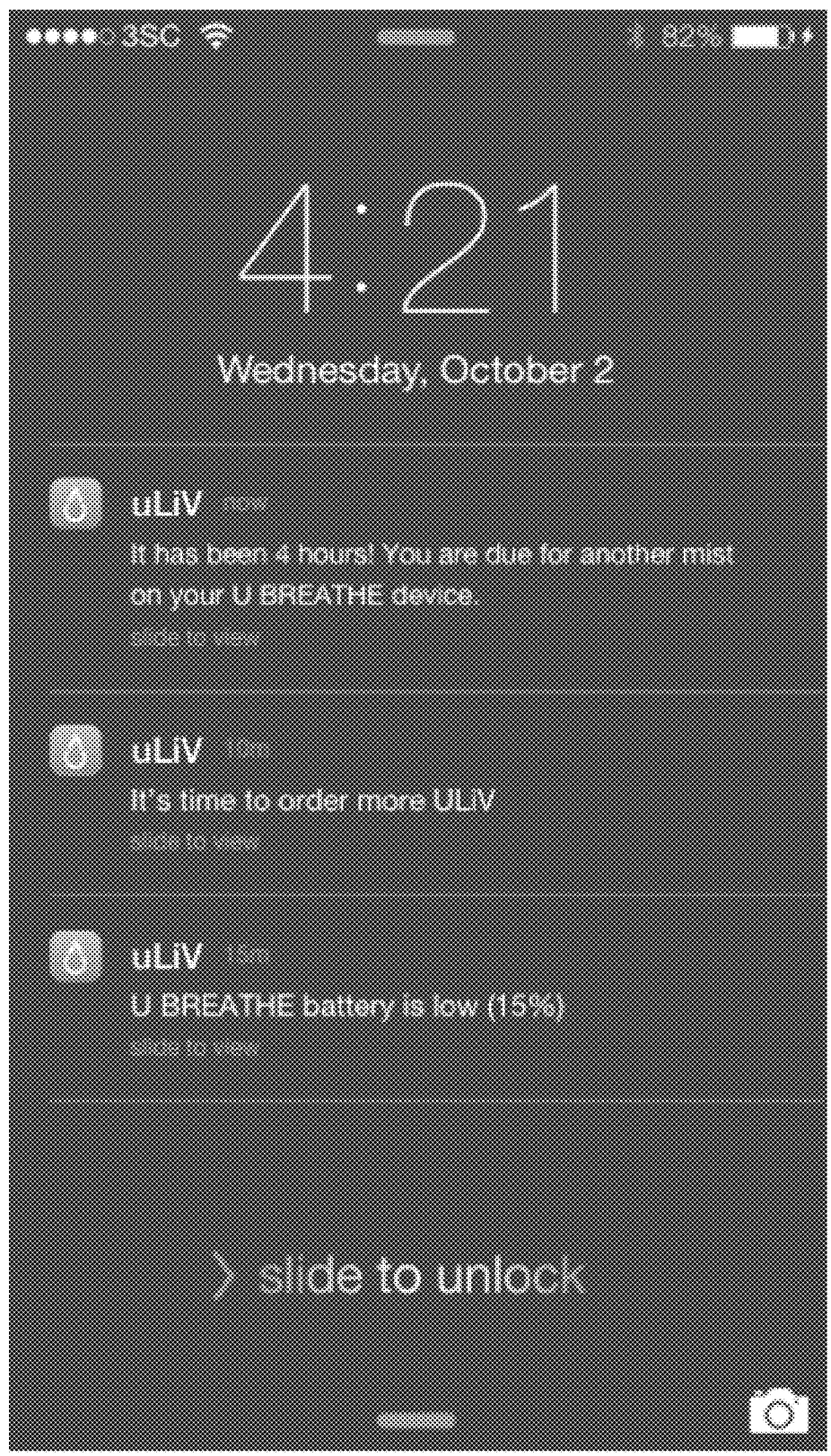

FIG. 35 shows an example of a user's overview screen. This may include a chart of inhalation device use over several days. The overview may be for a day, a week, a month, or other time period. The user can then drill-down to obtain more detailed information, such as shown in FIG. 36. FIG. 37 shows an example of a "last used" screen. More detailed information can be viewed, as shown in FIG. 38. The system also may provide alerts, warnings, and other messages to the user, as seen in FIG. 39.

In order to provide a context for the various aspects of the invention, the following discussion provides a brief, general description of a suitable computing environment in which the various aspects of the present invention may be implemented. A computing system environment is one example of a suitable computing environment, but is not intended to suggest any limitation as to the scope of use or functionality of the invention. A computing environment may contain any one or combination of components discussed below, and may contain additional components, or some of the illustrated components may be absent. Various embodiments of the invention are operational with numerous general purpose or special purpose computing systems, environments or configurations. Examples of computing systems, environments, or configurations that may be suitable for use with various embodiments of the invention include, but are not limited to, personal computers, laptop computers, computer servers, computer notebooks, hand-held devices, microprocessor-based systems, multiprocessor systems, TV set-top boxes and devices, programmable consumer electronics, cell phones, personal digital assistants (PDAs), tablets, smart phones, touch screen devices, smart TV, internet enabled appliances, internet enabled security systems, internet enabled gaming systems, internet enabled watches; internet enabled cars (or transportation), network PCs, minicomputers, mainframe computers, embedded systems, virtual systems, distributed computing environments, streaming environments, volatile environments, and the like.

Embodiments of the invention may be implemented in the form of computer-executable instructions, such as program code or program modules, being executed by a computer, virtual computer, or computing device. Program code or modules may include programs, objects, components, data elements and structures, routines, subroutines, functions and the like. These are used to perform or implement particular tasks or functions. Embodiments of the invention also may be implemented in distributed computing environments. In such environments, tasks are performed by remote processing devices linked via a communications network or other data transmission medium, and data and program code or modules may be located in both local and remote computer storage media including memory storage devices such as, but not limited to, hard drives, solid state drives (SSD), flash drives, USB drives, optical drives, and internet-based storage (e.g., "cloud" storage).

In one embodiment, a computer system comprises multiple client devices in communication with one or more server devices through or over a network, although in some cases no server device is used. In various embodiments, the network may comprise the Internet, an intranet, Wide Area Network (WAN), or Local Area Network (LAN). It should be noted that many of the methods of the present invention are operable within a single computing device.

A client device may be any type of processor-based platform that is connected to a network and that interacts with one or more application programs. The client devices each comprise a computer-readable medium in the form of volatile and/or nonvolatile memory such as read only memory (ROM) and random access memory (RAM) in communication with a processor. The processor executes computer-executable program instructions stored in memory. Examples of such processors include, but are not limited to, microprocessors, ASICs, and the like.

Client devices may further comprise computer-readable media in communication with the processor, said media storing program code, modules and instructions that, when executed by the processor, cause the processor to execute the program and perform the steps described herein. Computer readable media can be any available media that can be accessed by computer or computing device and includes both volatile and nonvolatile media, and removable and non-removable media. Computer-readable media may further comprise computer storage media and communication media. Computer storage media comprises media for storage of information, such as computer readable instructions, data, data structures, or program code or modules. Examples of computer-readable media include, but are not limited to, any electronic, optical, magnetic, or other storage or transmission device, a floppy disk, hard disk drive, CD-ROM, DVD, magnetic disk, memory chip, ROM, RAM, EEPROM, flash memory or other memory technology, an ASIC, a configured processor, CDROM, DVD or other optical disk storage, magnetic cassettes, magnetic tape, magnetic disk storage or other magnetic storage devices, or any other medium from which a computer processor can read instructions or that can store desired information. Communication media comprises media that may transmit or carry instructions to a computer, including, but not limited to, a router, private or public network, wired network, direct wired connection, wireless network, other wireless media (such as acoustic, RF, infrared, or the like) or other transmission device or channel. This may include computer readable instructions, data structures, program modules or other data in a modulated data signal such as a carrier wave or other transport mechanism. Said transmission may be wired, wireless, or both. Combinations of any of the above should also be included within the scope of computer readable media. The instructions may comprise code from any computer-programming language, including, for example, C, C++, C#, Visual Basic, Java, and the like.

Components of a general purpose client or computing device may further include a system bus that connects various system components, including the memory and processor. A system bus may be any of several types of bus structures, including, but not limited to, a memory bus or memory controller, a peripheral bus, and a local bus using any of a variety of bus architectures. Such architectures include, but are not limited to, Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing and client devices also may include a basic input/output system (BIOS), which contains the basic routines that help to transfer information between elements within a computer, such as during start-up. BIOS typically is stored in ROM. In contrast, RAM typically contains data or program code or modules that are accessible to or presently being operated on by processor, such as, but not limited to, the operating system, application program, and data.

Client devices also may comprise a variety of other internal or external components, such as a monitor or display, a keyboard, a mouse, a trackball, a pointing device, touch pad, microphone, joystick, satellite dish, scanner, a disk drive, a CD-ROM or DVD drive, or other input or output devices. These and other devices are typically connected to the processor through a user input interface coupled to the system bus, but may be connected by other interface and bus structures, such as a parallel port, serial port, game port or a universal serial bus (USB). A monitor or other type of display device is typically connected to the system bus via a video interface. In addition to the monitor, client devices may also include other peripheral output devices such as speakers and printer, which may be connected through an output peripheral interface.

Client devices may operate on any operating system capable of supporting an application of the type disclosed herein. Client devices also may support a browser or browser-enabled application. Examples of client devices include, but are not limited to, personal computers, laptop computers, personal digital assistants, computer notebooks, hand-held devices, cellular phones, mobile phones, smart phones, pagers, digital tablets, Internet appliances, and other processor-based devices. Users may communicate with each other, and with other systems, networks, and devices, over the network through the respective client devices.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art.

What is claimed is:

1. A system for managing inhalant devices, comprising:
a personal, portable nebulizer or vaporization device with an atomization chamber, a piezoelectric transducer for nebulization or vaporization, an ampoule holding chamber configured to hold a substance-containing ampoule, and a first mouth port from which a user inhales a nebulized or vaporized substance, wherein the first mouth port is in fluid communication with a first air conduit and the atomization chamber is separate from the ampoule;

wherein the portable nebulizer or vaporization device comprises a main body and a mouthpiece, wherein the mouthpiece is hingedly attached to the main body;

wherein the atomization chamber is integral within the mouthpiece;

wherein the piezoelectric transducer is located in the atomization chamber;
a plurality of ampoules, each ampoule containing a substance comprising one or more therapeutic, homeopathic, or naturopathic formulations, remedies, or serums, further wherein each ampoule is coded with information about the contained substance;
wherein the ampoule holding chamber is located is located below the mouthpiece and has an opening in which the ampoule is inserted;
wherein the mouthpiece closes the ampoule chamber opening when in use and wherein the substance from the ampoule is delivered to the piezoelectric transducer via a pump;
at least one breath analysis device with a detection chamber, a second mouth port into which a user exhales, a second air conduit in fluid communication with the second mouth port, and one or more transducers or sensors disposed in or in proximity to the detection chamber, wherein the first mouth port is separate from the second mouth port and not in fluid communication therewith, and the first air conduit is separate from the second air conduit and not in fluid communication therewith; and
a mobile computing device with a microprocessor and a wireless communications chip; wherein the mobile computing device is separate from the personal, portable nebulizer or vaporizer or the at least one breath analysis device, and wherein the microprocessor is programmed to:
store data about an individual user, said data comprising identification data and health data;
receive in real time, via electronic communications from the personal nebulizer or vaporization device, the coded information from an ampoule inserted into the nebulizer or vaporization device;
determine information about the substance contained in the inserted ampoule from the received coded information;
receive in real time, via wireless communications from the personal nebulizer or vaporization device, use information about the individual user's use of the substance contained in the inserted ampoule in conjunction with the personal nebulizer or vaporization device, wherein said use information includes duration of use and quantity of substance used;
update the individual user's health data with the use information and substance information;
receive in real time, via wireless communications from the at least one breath analysis device, a breath analysis result from a breath analysis test for the user performed with the at least one breath analysis device;
after receiving the breath analysis result, determine in real time, based at least in part of the breath analysis result, the type of substance and the dosing of said substance to be administered to said user through said personal nebulizer or vaporization device, wherein the breath analysis result comprises one or more of breath airflow and pressure; and
after determining the type and dosing, administer in real time said substance to the user through said personal nebulizer or vaporization device.

2. The system of claim 1, wherein one or more of said plurality of ampoules comprises an RFID chip, and the personal nebulizer or vaporization device comprises an RFID reader.

3. The system of claim 1, wherein the coded information is printed on the ampoule, and is readable by a scanner contained in the personal nebulizer or vaporization device.

4. The system of claim 1, wherein the microprocessor is further programmed to:
determine a health-related recommendation for the individual user.

5. The system of claim 4, wherein the health-related recommendation comprises a recommendation for a substance or substances to be used in the personal nebulizer or vaporization device.

6. The system of claim 5, wherein the microprocessor is further programmed to:
display the health-related recommendation for the individual user on the mobile communication device.

7. The system of claim 1, wherein said atomization chamber comprises one or more piezoelectric transducers or atomizers configured to vaporize or atomize the substance with sonic or ultrasonic energy.

8. The system of claim 1, the personal nebulizer or vaporization device further comprising:
at least one mouthpiece with an orifice; and
a conduit extending between the atomization chamber and the orifice.

9. The system of claim 8, wherein the at least one mouthpiece is removably attached to the main body.

10. The system of claim 1, the personal nebulizer or vaporization device further comprising a plurality of internal ultraviolet light sources configured to provide ultraviolet light inside the atomization chamber or conduit, or both.

11. The system of claim 1, the personal nebulizer or vaporization device further comprising a wireless communications chip.

12. The system of claim 1, the personal nebulizer or vaporization device further comprising one or more communications ports.

13. The system of claim 1, further comprising a cable adapted to attach the at least one breath analysis device to the mobile computing device.

14. The system of claim 1, said at least one breath analysis device further comprising a wireless communications chip.

15. The system of claim 14, wherein the mobile computing device, the personal nebulizer or vaporization device, and the at least one breath analysis device intercommunicate using short-range wireless communications.

* * * * *